United States Patent
Kysela

(10) Patent No.: US 9,943,598 B2
(45) Date of Patent: Apr. 17, 2018

(54) NANOPARTICLES WITH ATTACHED DNA REPAIR INHIBITORS AND NUCLEAR LOCALISATION SIGNAL ELEMENTS

(71) Applicant: The University of Birmingham, West Midlands (GB)

(72) Inventor: Boris Kysela, West Midlands (GB)

(73) Assignee: THE UNIVERSITY OF BIRMINGHAM EDGBASTON, Birmingham (GB)

( * ) Notice: Subject to any disclaimer, the term of this patent is extended or adjusted under 35 U.S.C. 154(b) by 405 days.

(21) Appl. No.: 14/403,804

(22) PCT Filed: May 28, 2013

(86) PCT No.: PCT/GB2013/051401
§ 371 (c)(1),
(2) Date: Nov. 25, 2014

(87) PCT Pub. No.: WO2013/179014
PCT Pub. Date: Dec. 5, 2013

(65) Prior Publication Data
US 2015/0119624 A1    Apr. 30, 2015

(30) Foreign Application Priority Data
May 29, 2012 (GB) .................... 1209517.0

(51) Int. Cl.
*A61K 41/00* (2006.01)
*A61N 5/10* (2006.01)
(Continued)

(52) U.S. Cl.
CPC .......... *A61K 41/0038* (2013.01); *A61K 38/16* (2013.01); *A61K 47/6923* (2017.08);
(Continued)

(58) Field of Classification Search
CPC .......... A61K 47/48884; A61K 41/0038; A61K 38/16; A61K 47/48861; C07K 14/4702; A61N 2005/1098; A61N 5/10
See application file for complete search history.

(56) References Cited

U.S. PATENT DOCUMENTS

| 6,645,464 B1 * | 11/2003 | Hainfeld | A61K 41/0038 424/1.11 |
| 2007/0110756 A1 * | 5/2007 | Reinberg | A61K 38/17 424/155.1 |

(Continued)

FOREIGN PATENT DOCUMENTS

| WO | 2008/054726 | 5/2008 |
| WO | 2010/121368 | 10/2010 |

OTHER PUBLICATIONS

O Connor MJ, Martin NMB, and Smith GCM. "Targeted cancer therapies based on the inhibition of DNA strand break repair". Oncogene (2007) 26, 7816-7824.*

(Continued)

*Primary Examiner* — Christine H Matthews
*Assistant Examiner* — Joshua D Lannu
(74) *Attorney, Agent, or Firm* — Brannon Sowers & Cracraft PC

(57) ABSTRACT

A radio- or chemo-sensitizing compound is described herein. The compound comprises a nanoparticle and attached to the nanoparticle;
 (i) a DNA repair inhibitor; and
 (ii) a nuclear localization signal element (NLS);
each optionally attached via one or more linker moieties.

22 Claims, 28 Drawing Sheets

(51) Int. Cl.
 A61K 38/16 (2006.01)
 C07K 14/47 (2006.01)
 A61K 47/69 (2017.01)
(52) U.S. Cl.
 CPC ............ *A61K 47/6929* (2017.08); *A61N 5/10* (2013.01); *C07K 14/4702* (2013.01); *A61N 2005/1098* (2013.01)

(56) References Cited

U.S. PATENT DOCUMENTS

2009/0148535 A1* 6/2009 Bamdad ............... A61K 9/5115
 424/499
2009/0263491 A1* 10/2009 Kreuter ................ A61K 9/0085
 424/497
2011/0268803 A1* 11/2011 Prud'homme ....... A61K 31/437
 424/489

OTHER PUBLICATIONS

Tkachenko AG, Xie H, Coleman D, Glomm W, Ryan J, Anderson MF, Franzen S, and Feldheim DL. "Multifuncitonal Gold Nanoparticle-Peptide Complexes for Nuclear Targeting". J. Am. Chem. Soc. 2003, 125, pp. 4700-4701.*

PCT Search Report prepared for PCT/GB2013/051401, dated Aug. 6, 2013.

Liu, Y., & Franzen, S. (2008). Factors determining the efficacy of nuclear delivery of antisense oligonucleotides by gold nanoparticles. Bioconjugate chemistry, 19(5), 1009-1016.

Sánchez-Pérez, Isabel. "DNA repair inhibitors in cancer treatment." Clinical and Translational Oncology 8.9 (2006): 642-646.

Quan, Qimeng, et al. "HSA coated iron oxide nanoparticles as drug delivery vehicles for cancer therapy." Molecular pharmaceutics 8.5 (2011): 1669-1676.

Ahamed, Maqusood, et al. "DNA damage response to different surface chemistry of silver nanoparticles in mammalian cells." Toxicology and applied pharmacology 233.3 (2008): 404-410.

Berry, C. C., et al. "Notice of Violation of IEEE Publication Principles Nuclear Localization of HIV-1 Tat Functionalized Gold Nanoparticles." IEEE transactions on nanobioscience 6.4 (2007): 262-269.

Kang, Bin, Megan A. Mackey, and Mostafa A. El-Sayed. "Nuclear targeting of gold nanoparticles in cancer cells induces DNA damage, causing cytokinesis arrest and apoptosis." Journal of the American Chemical Society 132.5 (2010): 1517-1519.

* cited by examiner

Controls, 30Gy

Gold A1 NPs targeted cells, 30Gy

SEQUENCE LISTING

<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Lys Glu Glu Ser Leu Ala Asp Asp Leu
1               5

<210> SEQ ID NO 2
<211> LENGTH: 11
<212> TYPE: PRT
<213> ORGANISM: Homo sapiens

```
<400> SEQUENCE: 2

Glu Gly Gly Asp Val Asp Asp Leu Asp Met Ile
1               5                   10

<210> SEQ ID NO 3
<211> LENGTH: 14
<212> TYPE: PRT
<213> ORGANISM: Unknown
<220> FEATURE:
<223> OTHER INFORMATION: M4 synthetic targeting sequence

<400> SEQUENCE: 3

Lys Lys Lys Lys Lys Lys Gly Gly Arg Gly Asp Met Phe Gly
1               5                   10

<210> SEQ ID NO 4
<211> LENGTH: 12
<212> TYPE: PRT
<213> ORGANISM: Adenovirus type 37

<400> SEQUENCE: 4

Gly Gly Phe Ser Thr Ser Leu Arg Ala Arg Lys Ala
1               5                   10

<210> SEQ ID NO 5
<211> LENGTH: 14
<212> TYPE: PRT
<213> ORGANISM: Unknown
<220> FEATURE:
<223> OTHER INFORMATION: 3 repeat Gold Binding Peptide repeat sequence

<400> SEQUENCE: 5

Met His Gly Lys Thr Gln Ala Thr Ser Gly Thr Ile Gln Ser
1               5                   10

<210> SEQ ID NO 6
<211> LENGTH: 28
<212> TYPE: PRT
<213> ORGANISM: Unknown
<220> FEATURE:
<223> OTHER INFORMATION: M4 targetting NBS1 inhibition

<400> SEQUENCE: 6

Cys Ala Leu Asn Asn Lys Lys Lys Lys Lys Lys Gly Gly Arg Gly Asp
1               5                   10                  15

Met Phe Gly Lys Glu Glu Ser Leu Ala Asp Asp Leu
            20                  25

<210> SEQ ID NO 7
<211> LENGTH: 26
<212> TYPE: PRT
<213> ORGANISM: Unknown
<220> FEATURE:
<223> OTHER INFORMATION: Adenovirus NBS1 inhibition

<400> SEQUENCE: 7

Cys Ala Leu Asn Asn Gly Gly Phe Ser Thr Ser Leu Arg Ala Arg Lys
1               5                   10                  15

Ala Lys Glu Glu Ser Leu Ala Asp Asp Leu
            20                  25

<210> SEQ ID NO 8
<211> LENGTH: 5
<212> TYPE: PRT
<213> ORGANISM: Unknown
```

```
<220> FEATURE:
<223> OTHER INFORMATION: CALNN peptide

<400> SEQUENCE: 8

Cys Ala Leu Asn Asn
1               5
```

NANOPARTICLES WITH ATTACHED DNA REPAIR INHIBITORS AND NUCLEAR LOCALISATION SIGNAL ELEMENTS

CROSS-REFERENCE TO RELATED APPLICATIONS

This application is a U.S. national application under 37 C.F.R. § 371(b) of International Application Serial No. PCT/GB2013/051401 filed 28 May 2013, which claims the benefit under 35 U.S.C. § 119(a) of GB Application No. 1209517.0, filed on May 29, 2012, the entire disclosures of each of which are incorporated herein by reference.

The invention relates to radio- or chemo-sensitising compounds comprising a nanoparticle and attached to the nanoparticle a DNA repair inhibitor and a nuclear localisation signal element (NLS). Such compounds are used in the treatment of diseases, such as cancers.

Nanotechnology represents the area of science focused on the manipulation of atoms and molecules that leads to new structures in the nanometer scale range. These structures often gain unique and unexpected properties. In cancer nanotechnology the focus is on development of nanoscale devices that can diagnose, deliver therapeutic agents, and monitor cancer treatment progress. Ideally, any imaging or therapeutic system would be exclusively targeted to the tumour cell clusters or tumour cell vasculature, preferably with the ability to do so at early stages of malignant transformation. The past decades had seen outstanding progress in our understanding of fundamental cancer biology and DNA damage responses (Risinger and Groden; Cancer Cell, 6: 539, 2004; O'Driscoll and Jeggo; Nat Rev Genet; 7: 45, 2006, Girard, Kysela et al; Hum Mol Genet 13:1, 2004, Weller, Kysela, Roy et al; Science 297:5527, 2002) but this development was not accompanied by comparable advances in the clinic. For example radiation therapy in humans benefited much more from technical progress and computerization rather than from knowledge-based manipulation of the biological responses of cancer cells to therapeutic radiation (Begg et al, Radiother Oncol, 86:295, 2008).

Nanoparticles can be used to introduce material into cells. The cells engulf and take the nanoparticles with any components attached to the particles.

The Applicants have recognised that this had the potential to promote the introduction of chemo-sensitising and radio-sensitising compounds into the cell. Many of these compounds need to be targeted at the cell nucleus to be effective. They therefore recognised that there was also a need to be able to target the compounds once they are within the cell to direct them to the cell nucleus.

The invention therefore provides a radio- or chemo-sensitising compound comprising a nanoparticle and attached to the nanoparticle; (i) a DNA repair inhibitor; and (ii) a nuclear localisation signal element (NLS); optionally attached to the nanoparticle via one or more linker moieties.

The nanoparticles are typically below 100 nm, typically 1-50 nm, 5-30 nm or 10-15 nm in diameter.

The DNA repair inhibitor acts to sensitise the cell to a radio or chemo-therapeutic agent.

The DNA repair inhibitor and NLS may be separately attached to the nanoparticle, optionally via a linker moiety. That is, the inhibitor and NLS may be attached to separate parts of the nanoparticle. Alternatively the DNA inhibitor may be attached to the nanoparticle, for example, via a linker moiety, and the NLS may be attached to the DNA repair inhibitor (for example as a fusion protein/peptide) or attached to a different part of the linker moiety, for example as a pendant moiety. Alternatively the NLS may be attached to the nanoparticle, for example via a linker moiety, and the DNA repair inhibitor may be attached to the NLS, or to the linker moiety (for example as a pendant moiety).

Many radio therapeutic agents, such as gamma rays or x-rays, and chemotherapeutic agents (for example as a fusion protein such as bleomycin), damage targeted cells inducing strand breaks to the DNA. Single-strand breaks occur where one half of the DNA double helix is broken. Such single-strand breaks are relatively easy to repair by the DNA repair systems within the cell. Double-strand breaks, however, which occur potentially opposite one another on the two strands of the DNA helix, are more difficult to repair. They are particularly problematic to the cell because they can lead to genome rearrangement. Three mechanisms exist to repair double-strand breaks (DSBs); non-homologous end joining, microhomology-mediated end joining and homologous recombination. If a strand break is not correctly repaired or the DNA double-strand break is not repaired at all, a cell will often die in the next mitosis.

Repair inhibitors are generally known in the art. Typically the inhibitor will be an inhibitor of DNA double-strand break repair as DSBs, as discussed above, are likely to kill or disable the cell being targeted by the compound. The DNA inhibitor may be NBS1 (Nijmegen Breakage Syndrome 1, Nibrin). This is a 754 amino acid protein identified as a member of the NBS1/hMre11/RAD50 double-strand DNA break repair complex. This complex recognises DNA damage and rapidly relocates to DSB sites and forms nuclear foci. A typical NBS1 sequence is KEESLADDL.

Fragments of this and indeed other DNA repair inhibitors, which still retain DNA repair inhibition activity, may also be used.

The DNA inhibitor may be Ku70 or a fragment thereof. Ku70 is protein encoded by the XRCC6. Protein together with Ku80, make up the Ku heterodimer, which binds to DBS ends and is involved in DNA repair. A synthetic peptide mimicking the domain of the Ku80 protein may be used (EGGDVDDLDMI) Kim et al J. Pharmacol. Exp. Therap. (2002) 303:353.

PARP1 (Poly [ADP-Ribose] Polymerase-1) modifies nuclear proteins by poly ADP-ribosylation. It is involved in DSB repair in conjunction with BRCA. Additionally, PARP1 is also involved in the repair of single-stranded DNA breaks. Alternatively, the main repair inhibitor may be H1x or a fragment thereof. A linker histone that is ubiquitously present in all somatic cells. See, for example, PCT/GB2011/051180, WO/2011/161457.

DNA phosphokinase inhibitors may also be used.

The NLS may be, for example, an adenoviral or SV40 NLS, or a synthetic sequence such as M4 targeting sequence. The M4 targeting sequence may be KKKKKKGGRGDMFG. The adenoviral NLS may be GGFSTSLRARKA.

A synthetic NLS may also be used. Synthetic NLS are generally known in the art. The M4 targeting sequence from the above is a synthetic peptide, the Adenoviral NLS is a naturally occurring targeting sequence.

The nanoparticles are typically metal nanoparticles, such as transition metal particles. These include gold, platinum or palladium, or mixtures thereof. An advantage of, for example, platinum and gold is that such particles can enhance the effects of ionising radiation via production of photoelectrons and Auger electrons (Zheng et al; Radiat. Res. (2008), 169:19, Hainfeld et al; Phys. Med. Biol. (2004), 49:N309, and Biston et al; Cancer Res. (2004), 64:2317). The ionising radiation may be tuned to allow the production of such electrons, thereby increasing the effect of the radiation on the cell targeted. The effect of the electrons produced by the radiation is dependent upon the close proximity to the DNA due to short predicted distances travelled by the secondary electrons responsible for the effects (Zheng et al (Supra) and Regulla et al (Rad. Res. (1998) 150:92). The presence of the NLS assists in targeting the nanoparticles to the nucleus of the cell, thereby assisting in localisation of the nanoparticles close to the DNA.

The peptide based DNA repair inhibitors and/or NLS may be attached via generally known systems onto the nanoparticle. For example, a linker moiety having affinity for the metal nanoparticle may be utilised. Such linker moieties include thio-containing linkers, such as thioctic acid, gold binding peptide 1 (Brown et al, Nat. Biotech. (1997), 15:269), 3R-GBP1 which contains 3 repeat sequence of MHGKTQATSGTIQS (Tamerler et al; Small (2006) 2:1372) which binds to both gold and platinum surfaces, CALNN peptide (Lévy R, J. Am. Chem. Soc. (2004) 126 (32), 10076-84).

One or more additional moieties may also be attached to the compound. The additional moieties may be attached, for example, directly to the nanoparticle utilising, for example, a linker moiety as described above, or alternatively attached to the DNA repair inhibitor, NLS, and/or their linker moieties. The one or more additional moieties may be selected from, for example, a chemotherapeutic agent, a DNA cross-linking agent, an imaging agent, a contrasting agent and a surface targeting agent. Two or more additional types of moieties may be used.

A chemotherapeutic agent may, for example, be an agent which induces DNA damage, such as DNA single or typically double-stranded breaks. Bleomycin, for example, is a glycopeptide antibiotic produced by the bacterium *Streptomyces verticillus*. This is generally known as an anti-cancer agent, the chemotherapeutic forms being primarily bleomycin $A_2$ and $B_2$. It works by causing breaks in DNA.

The chemotherapeutic agent may also be doxorubicin. Doxorubicin is an anthracycline antibiotic which is commonly used in the treatment of a wide range of cancers, and intercalates into DNA.

It may be used in combination with other chemotherapeutic agents, including bleomycin and calichaemycin. A still further chemotherapeutic agent may be Camptothecin. Camptothecin is a cytotoxic quinoline alkaloid which inhibits the DNA enzyme topoisomerase I. Camptothecin and two analogs (topotecan and irinotecan) have been used in cancer chemotherapy. Analogs of such compounds may also be used. Other agents include nitrogen mustards, temozolamide and cross-linking agents generally known in the art, including cis-platinins (Brown et. al., J. Am. Soc. (2012) 132, 4676-84).

The imaging agent may be a fluorescent dye, generally known in the art, such as fluorescein.

The contrasting agent may be gadolinium, iron oxide, manganese or other paramagnetic contrasting agents. These allow the targeting of the compounds to the site of the cancer to be confirmed.

The surface targeting agent may be a moiety that is capable of being specifically attached to a cancer cell. That moiety may, for example, be a ligand of a receptor found on the surface of the cancer cell. For example, vitamin receptors, such as folate receptors, are commonly over-expressed in many cancer cells. Hence the cell surface targeting agent may, for example, be a vitamin, such as folate (Leamon et al, J. Drug Target. (1999) 7:157). The advantages of being able to target the nanoparticles towards specific cells are that it assists in limiting toxic side effects to normal cells. For example, vitamin-linked molecules may be internalised by receptor-mediated endocytosis. The uptake of generally known folate-delivered cytotoxic drugs has been shown and they have promising effects in pre-clinical studies. The vitamin such as folate may be conjugated to peptides, for example, by standard solid-phase chemistry.

Compounds of the invention may be used in combination with one or more pharmaceutically acceptable carriers or diluents. It may be used as a medicament, for example for use in treating cancer.

Methods of treating cancer in a subject comprising administering a pharmaceutically effective amount of the compound according to the invention are also provided.

The compound may be administered intravenously, intramuscularly, intraperitoneally or orally. Brain tumours may be treated, for example, be perfusion through the skull beyond the blood-brain barrier.

The subject may additionally be subjected to radiotherapy. For example, where the compound comprises a metal nanoparticle, post administration of the compound the subject may be treated with radiotherapy from an ionising radiation source tuned to the absorption edge of the metal nanoparticle. This causes the nanoparticle to emit secondary electrons, as discussed above.

The ionising radiation source may, for example, be an x-ray source or synchrotron source.

The invention provides for example, the combination of a local increase in DNA damage by either DNA damaging agents attached to the same particle or by radiation via the metal of the nanoparticle itself. This is combined with local synergistic decrease in DNA repair in the same region of the nucleus damaged by the DNA damaging agents or radiation.

Further advantages of the invention, include the possible overcoming of drug resistance to chemotherapy in cancers, such as leukaemia. When leukaemia is treated, many patients have drug resistance due to blocking of the cell uptake pathway by the cancer cells. It is believed that utilising nanoparticles may assist in overcoming such resistance.

The invention will now be described by way of example only by reference to the following figures:

FIGS. 1a-1d: Targeted vs. non-targeted NPs delivery in MRC5 normal human fibroblasts. Panels A and C: The ESRF nanoimaging station zinc line provides essential microstructural information from which the cell nucleus and cytoplasmic regions can be easily distinguished in relation to gold (or platinum) X-ray fluorescence signals (also next figure). Panel B: Gold line signal in cells exposed to non-targeted NPs.

Panel D: Gold line signal in cells exposed to NPs targeted to the cell nucleus by a novel synthetic peptide consisting of gold attachment domain, nuclear targeting domain and DNA repair inhibition domain in tandem configuration—these results demonstrate that only targeted nanoparticles can reach cell nucleus.

FIGS. 2a-2d: Targeted NPs delivery in human tumour cell lines. Panels A and B: A549 lung adenocarcinoma cells, A: Zinc lines and B: Gold line. Panels C and D K562 human myeloid leukaemia suspension cell line, C: Zinc line and D: Gold line.

Panels B and D show the high presence of gold line signal in cells exposed to NPs targeted to the cell nucleus by a novel synthetic peptide consisting of gold attachment domain, nuclear targeting domain and DNA repair inhibition domain in tandem configuration—these results show that only targeted nanoparticles can reach cell nucleus and demonstrate the universality and high efficiency of payload delivery by the targeting peptide construct for both fibroblastoid and lymphoblastoid tumour cell populations.

Figure 1A:
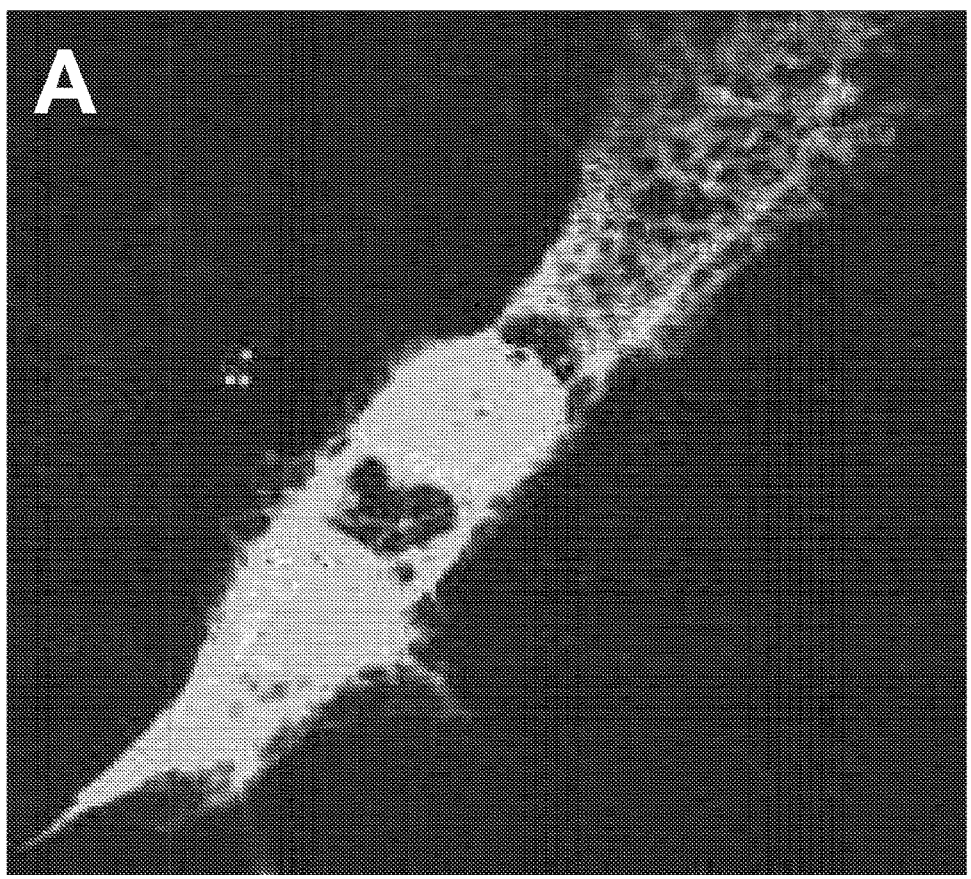
FIGS. 1a-1d: Targeted vs. non-targeted NPs delivery in MRC5 normal human fibroblasts.
Figure 1B:
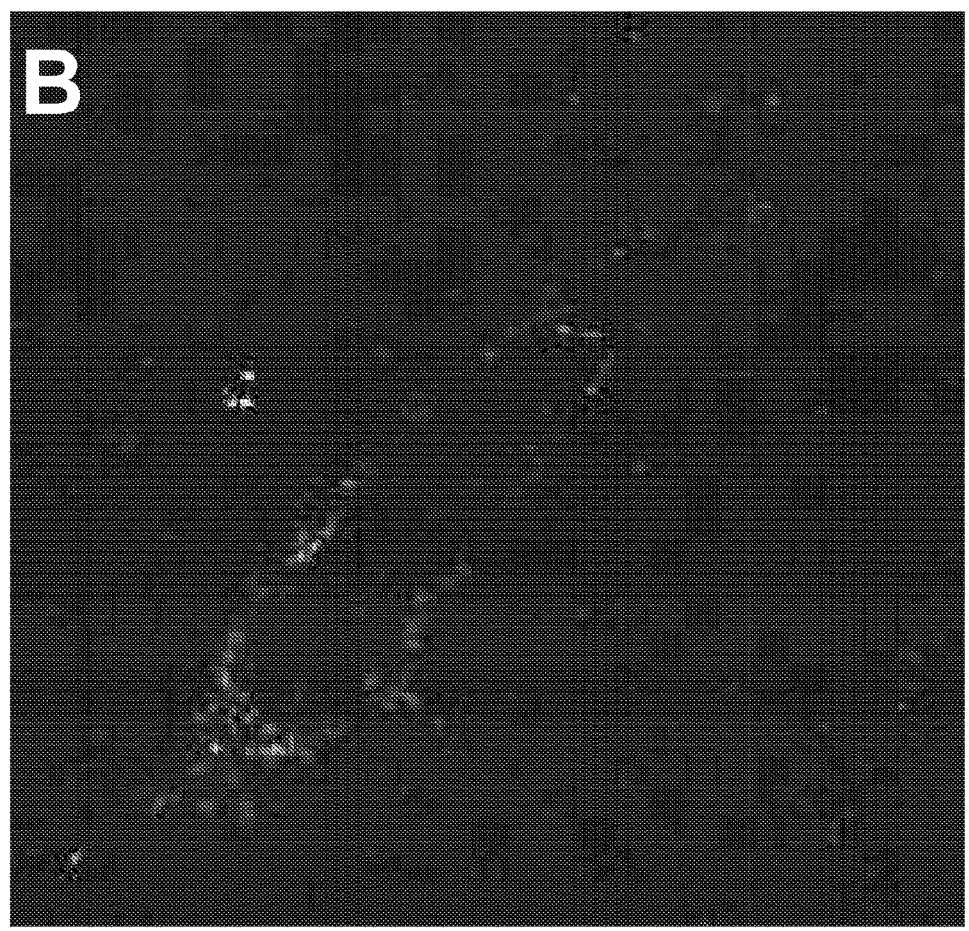
Figure 1C:
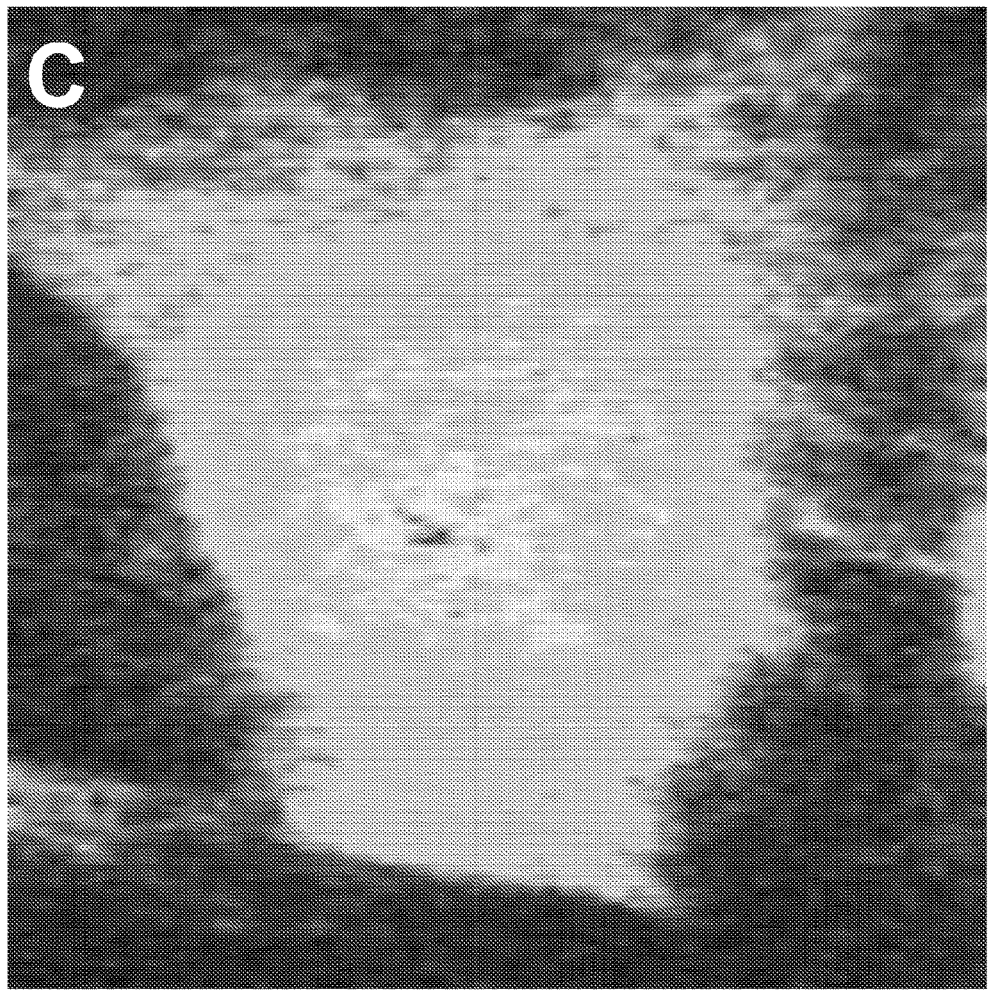
Figure 1D:
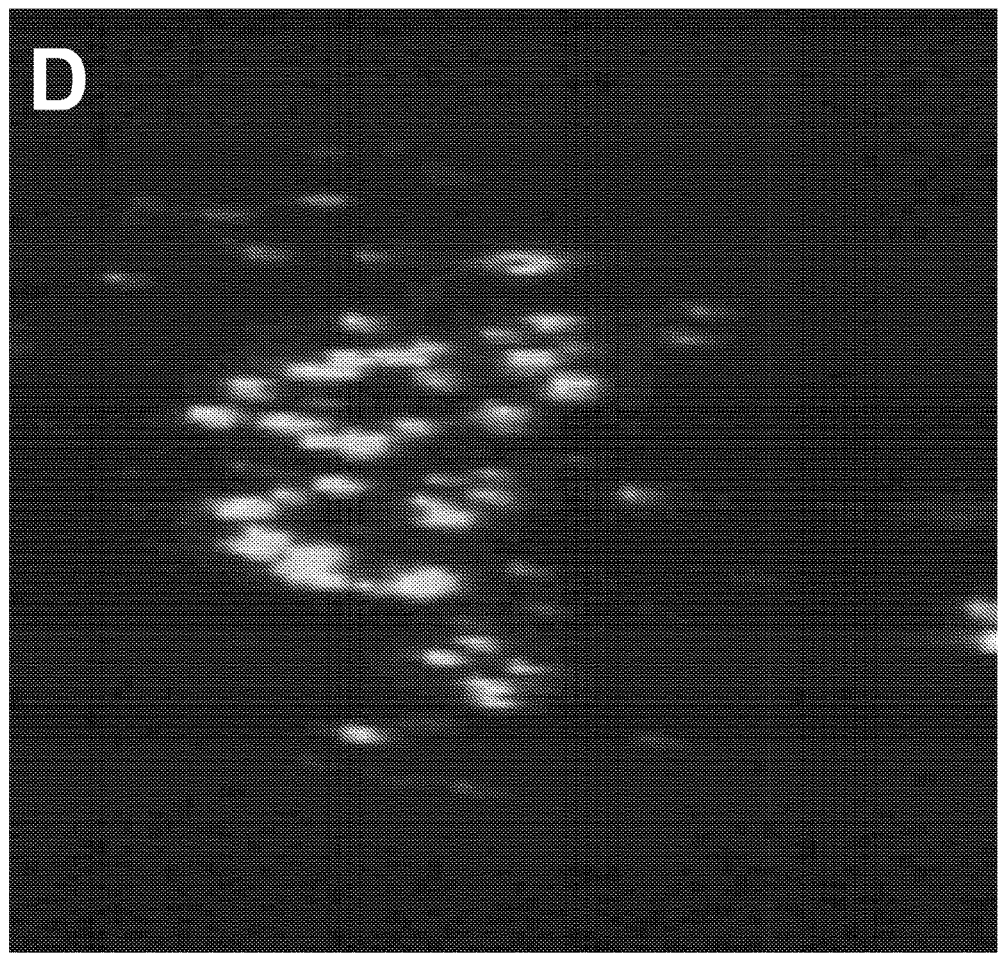
Figure 2A:
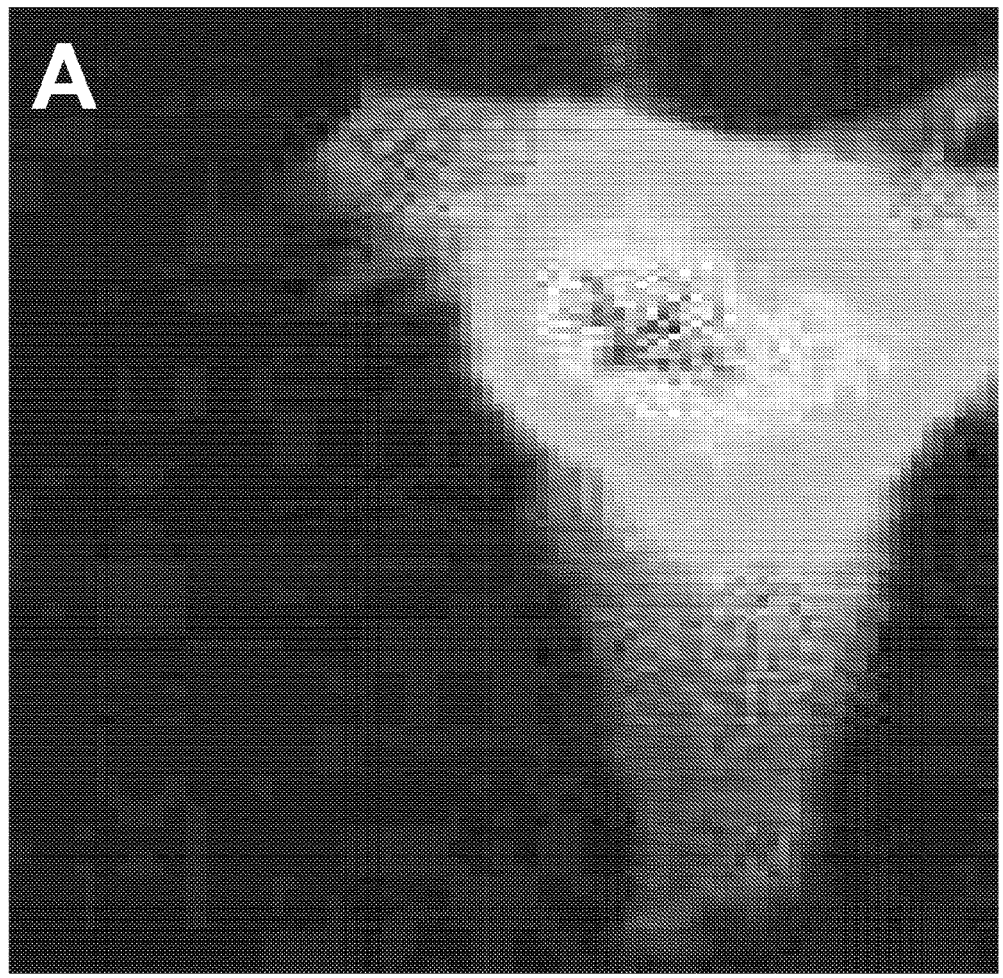
FIGS. 2a-2d: Targeted NPs delivery in human tumour cell lines.
Figure 2B:
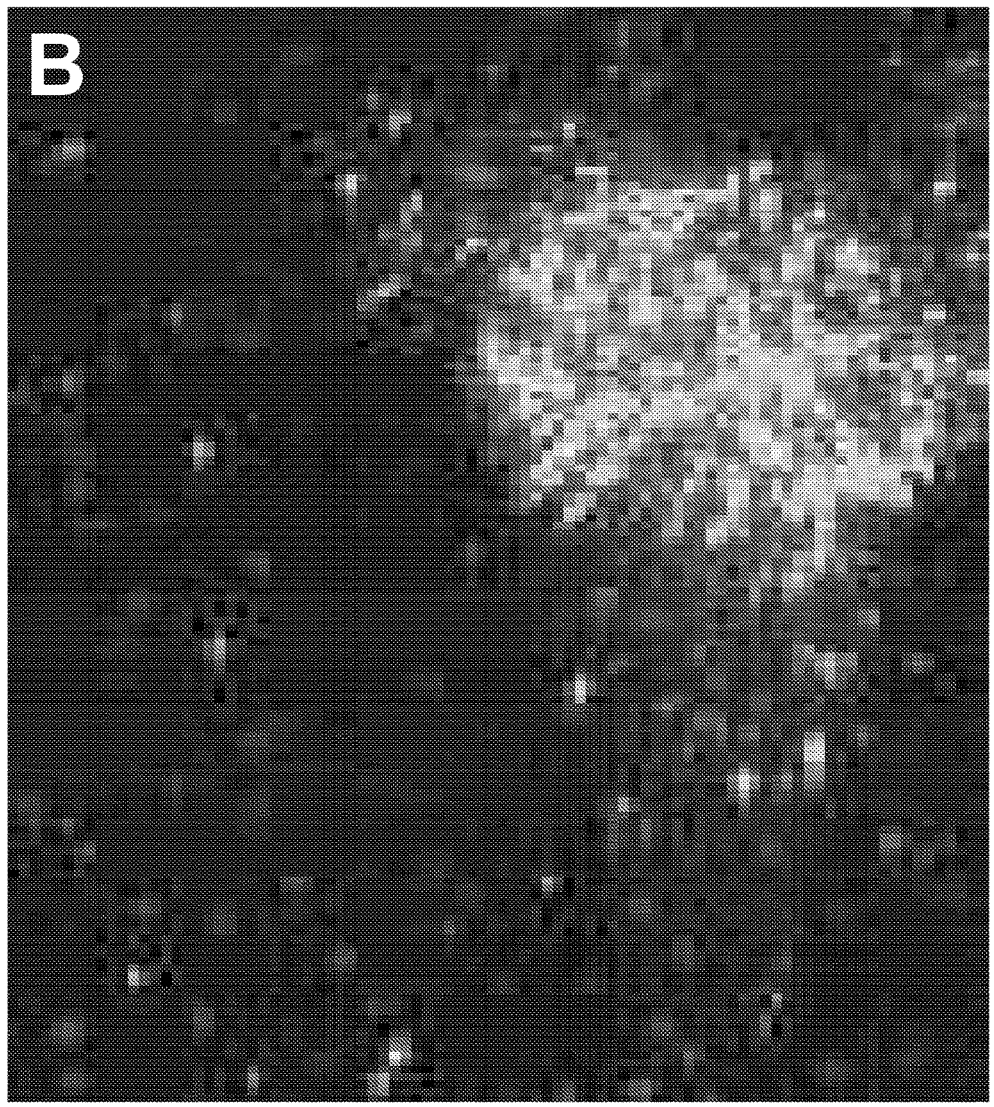
Figure 2C:
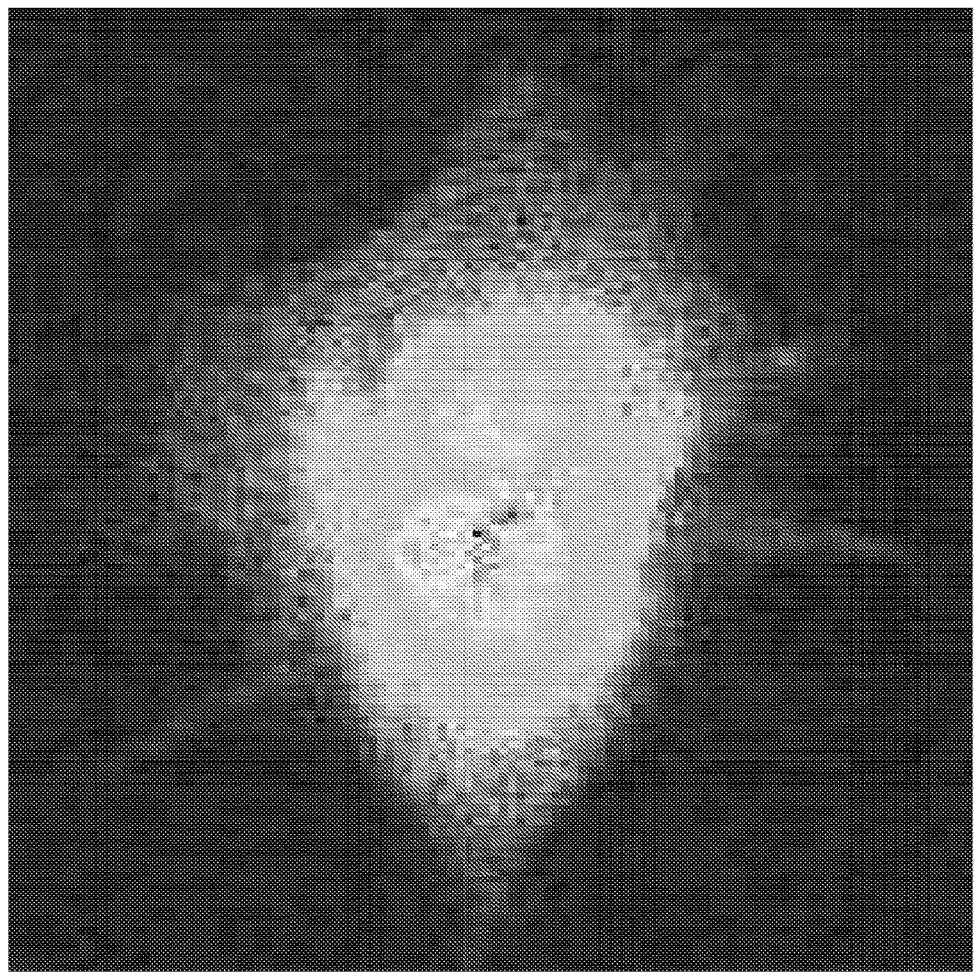
Figure 2D:
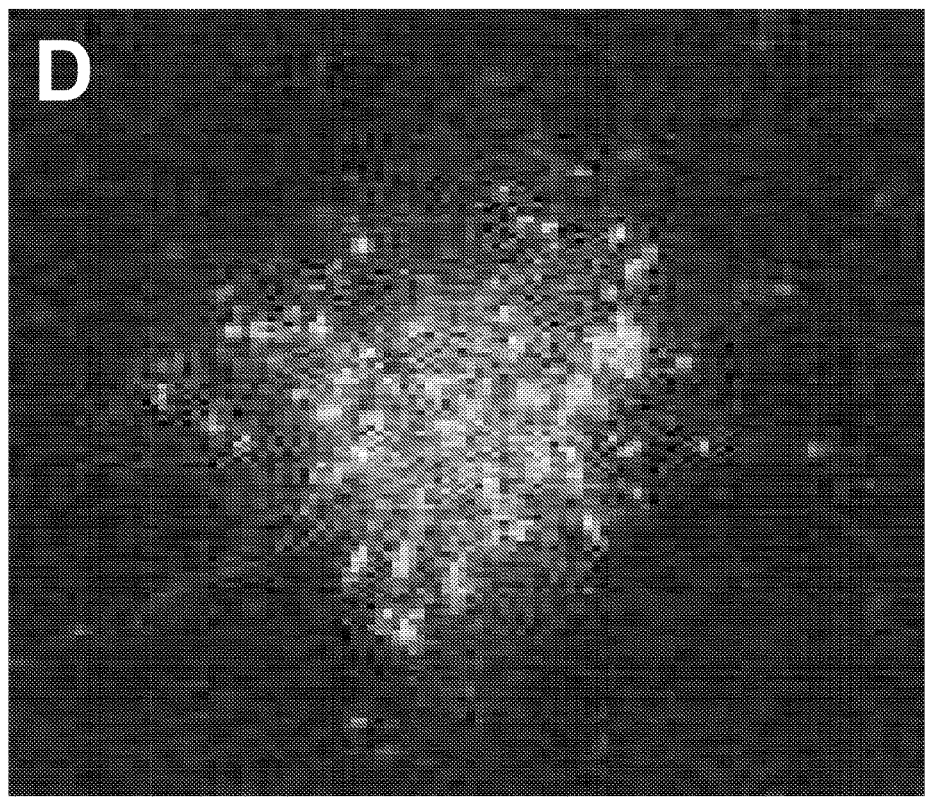
Figure 3:
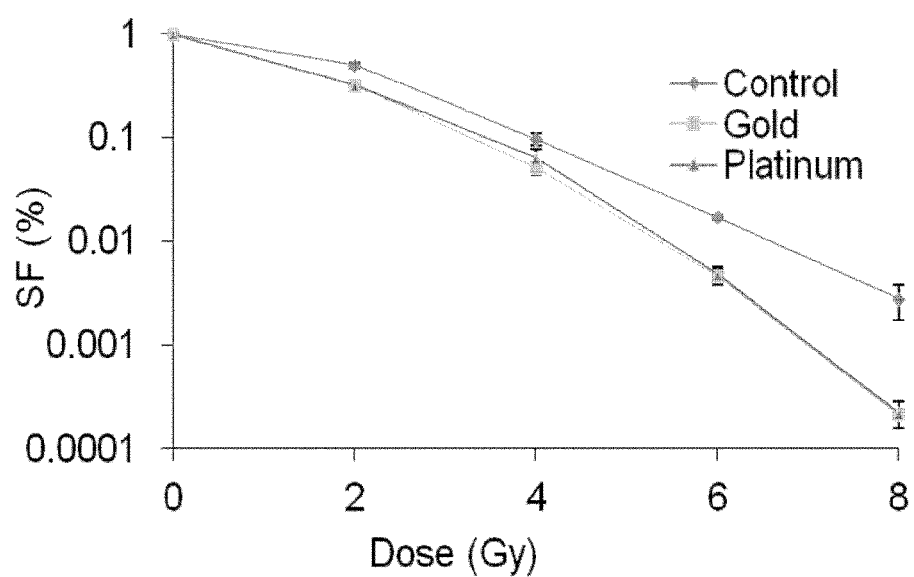
FIG. 3: Analysis of synergistic effect of targeted NPs and radiation on human cells.
Figure 4A:
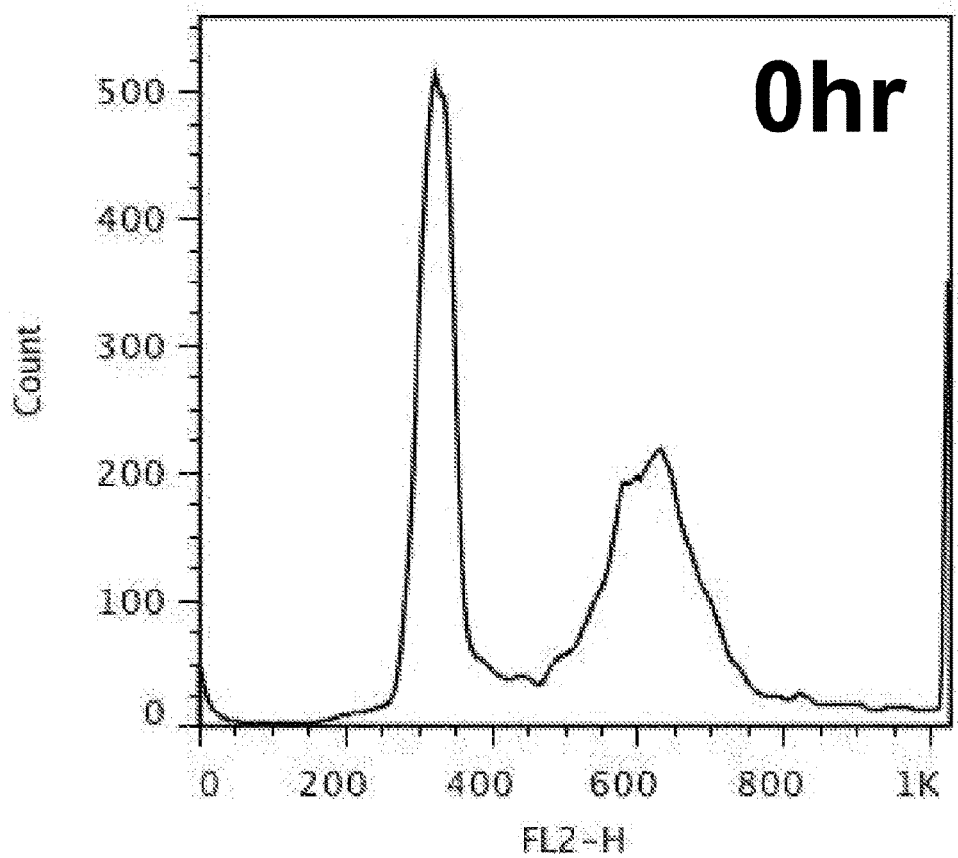
FIGS. 4a-4h: Flow cytometry analysis of the impact of targeted NPs on the cell cycle distribution in MRC5 normal human fibroblasts.
Figure 4B:
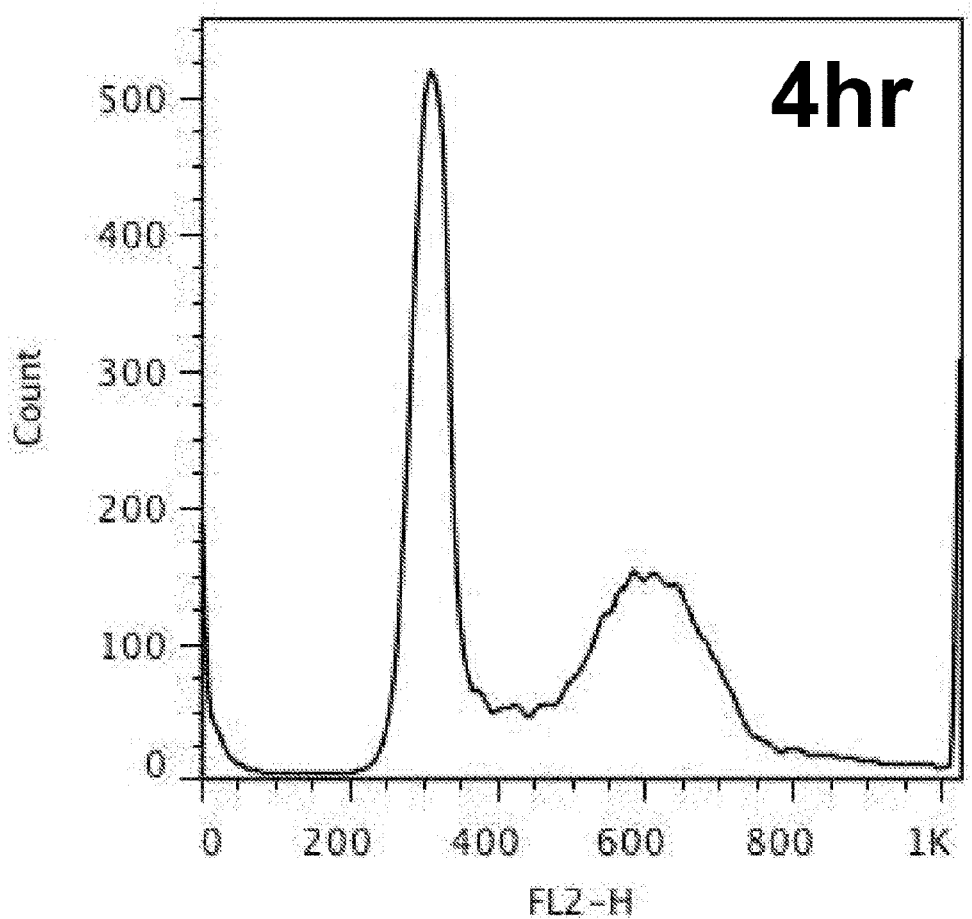
Figure 4C:
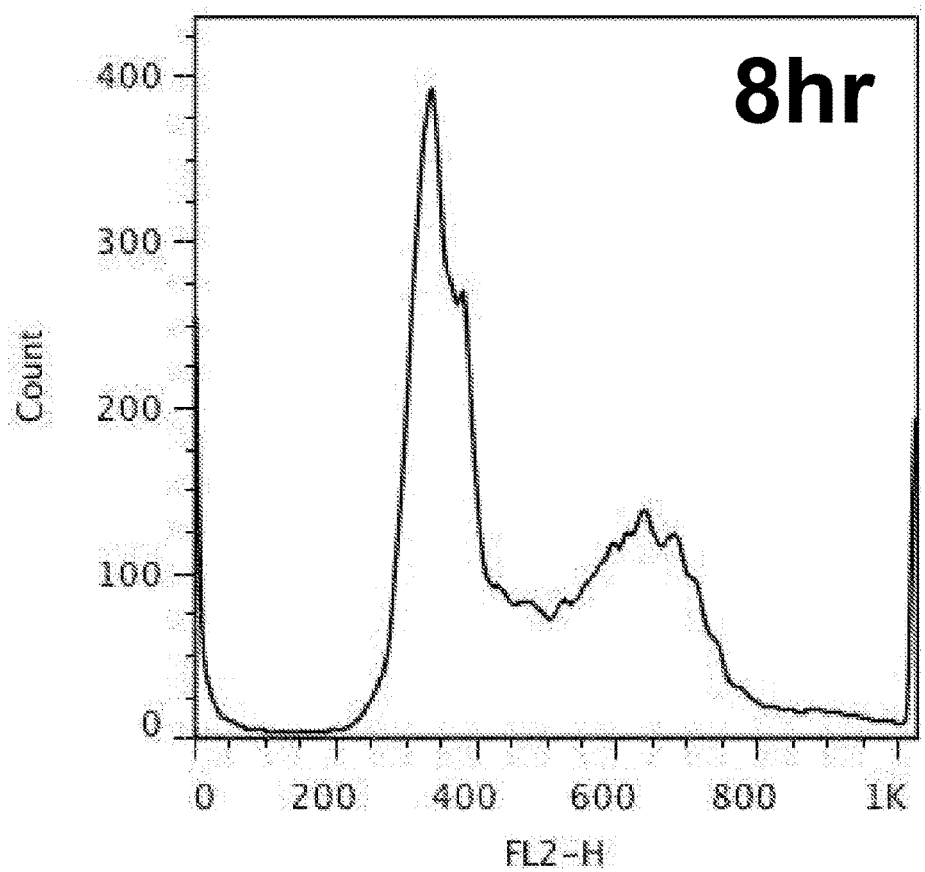
Figure 4D:
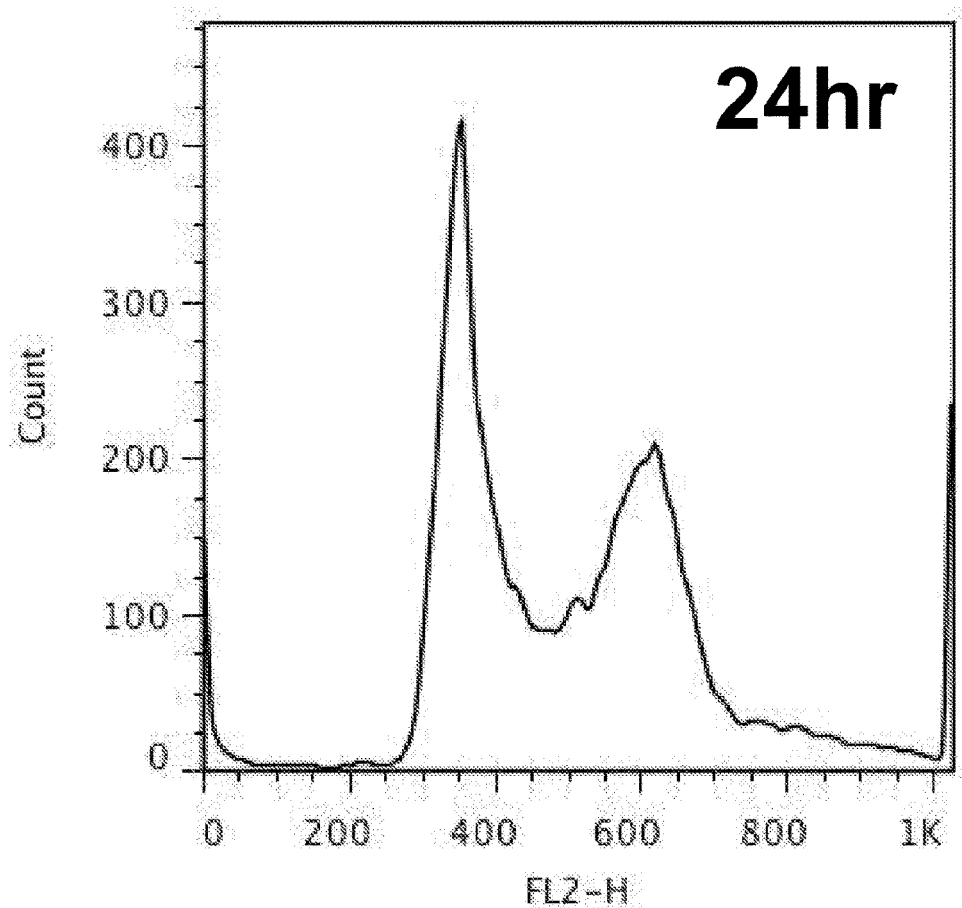
Figure 4E:
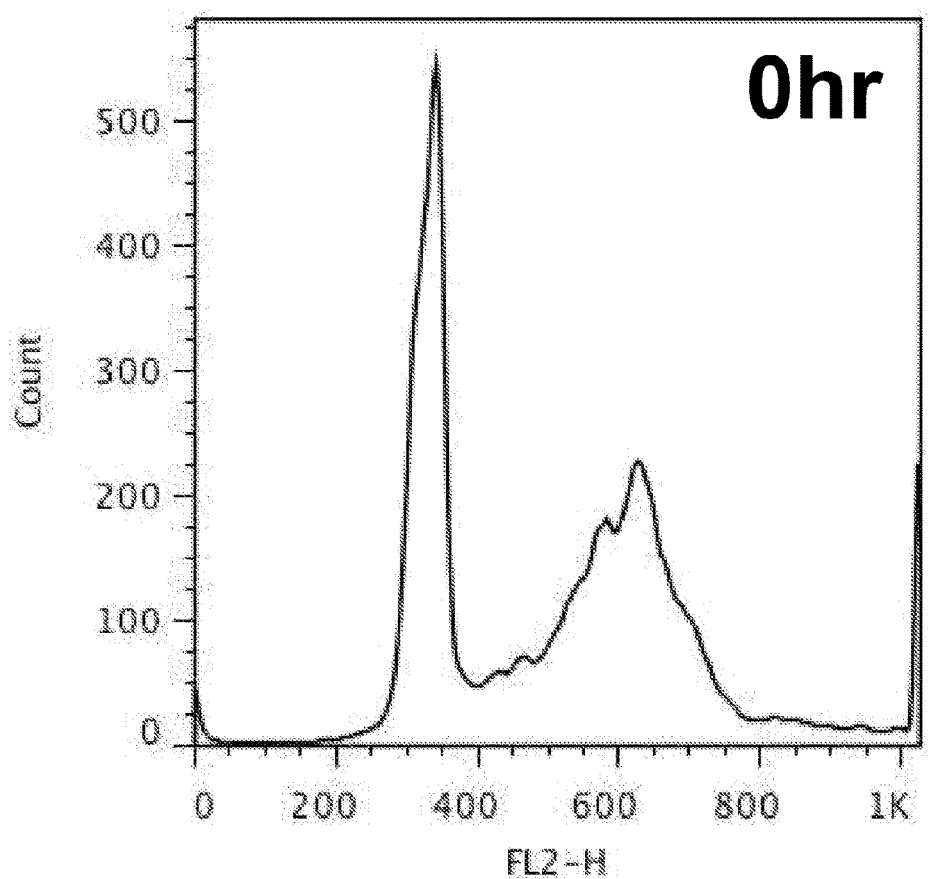
Figure 4F:
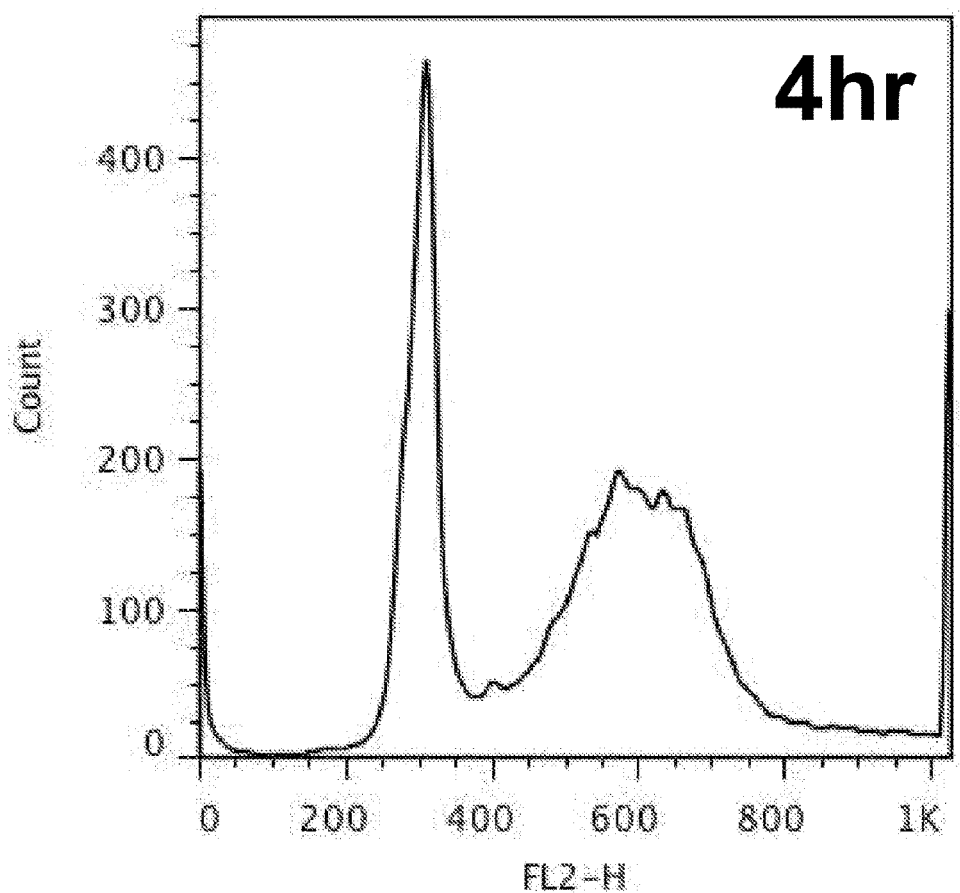
Figure 4G:
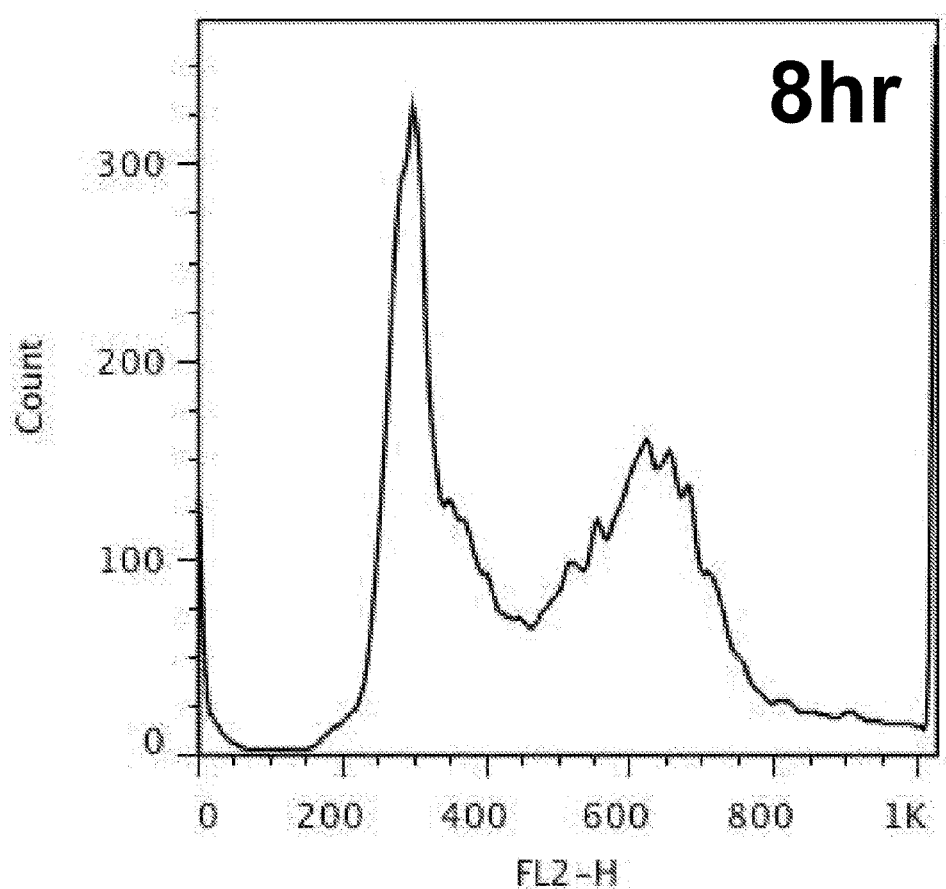
Figure 4H:
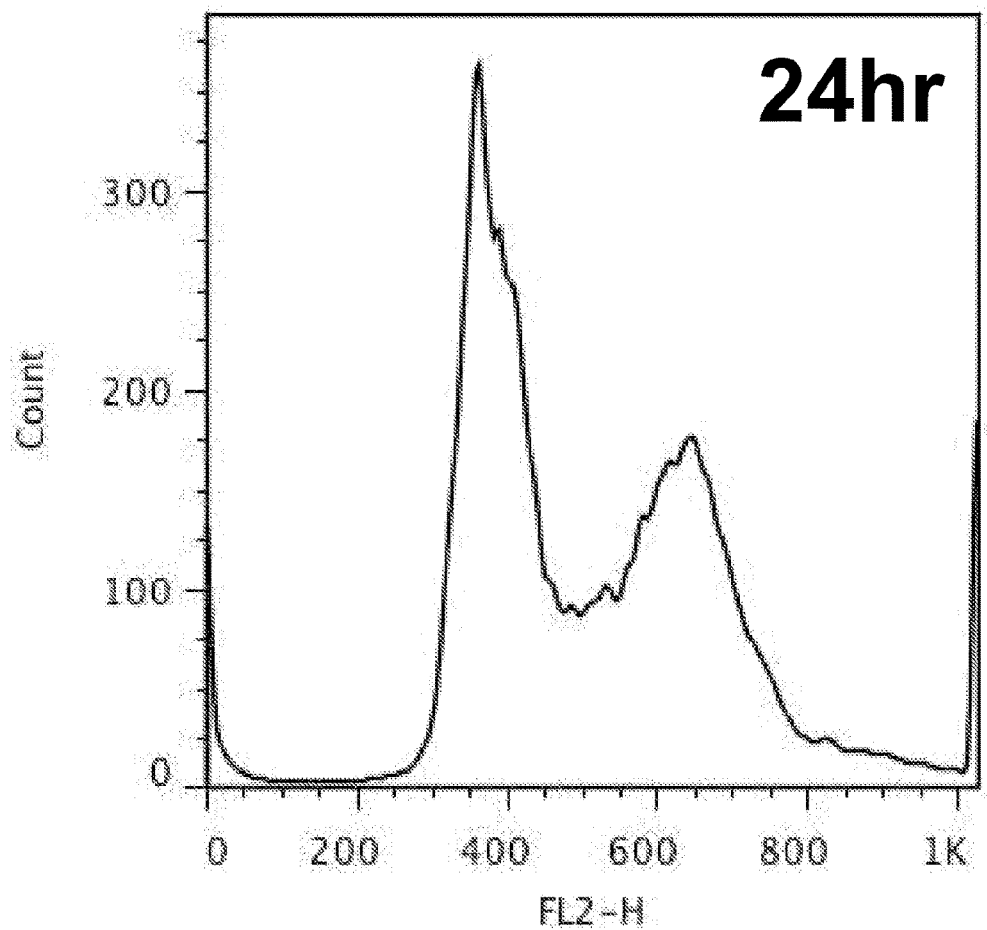

FIG. 3: Analysis of synergistic effect of targeted NPs and radiation on human cells. Panel A: Full clonogenic survival analysis of MRC5 normal human fibroblasts. Panel B: 2Gy survival fraction analysis in K562 human chronic myeloid leukaemia cells.

No enhancement of cell killing had been observed with non-targeting controls. These results demonstrate that only nanoparticles targeted to the cell nucleus by a novel synthetic peptide consisting of gold attachment domain, nuclear targeting domain and DNA repair inhibition domain in tandem configuration enhances the cell killing by radiation.

FIGS. 4a-4h: Flow cytometry analysis of the impact of targeted NPs on the cell cycle distribution in MRC5 normal human fibroblasts. Top row: Time course of cell cycle progression in unexposed controls. Bottom row: Time course of the cell cycle progression in cells exposed to targeted NPs under conditions identical to cell survival experiments. No changes in the cell cycle distribution have been observed between cells exposed to nanoparticles targeted to the cell nucleus by a novel synthetic peptide consisting of gold attachment domain, nuclear targeting domain and DNA repaid inhibition domain in tandem configuration and the control cells. These data strongly suggest that the enhancement in cell killing observed in the cell survival experiments is a result of increased DNA damage/decreased DNA repaid effect caused by nucleus-targeted nanoparticles.

Figure 5A:
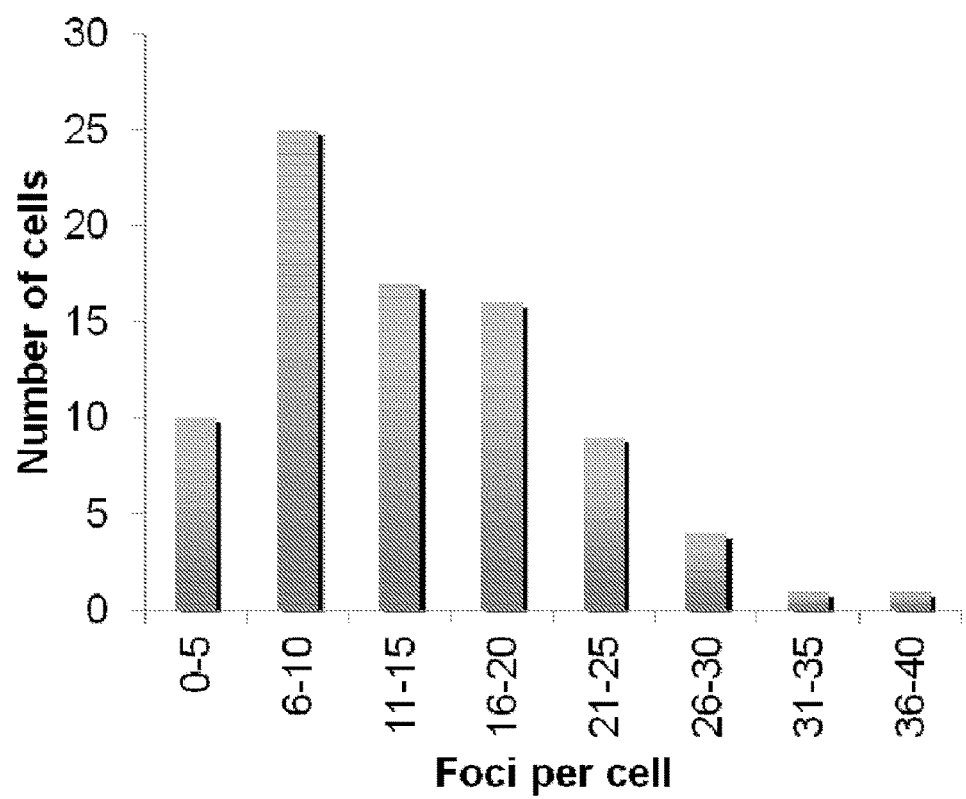
FIGS. 5a-5b: γH2AX foci analysis 24 h after radiation with 5Gy.
Figure 5B:
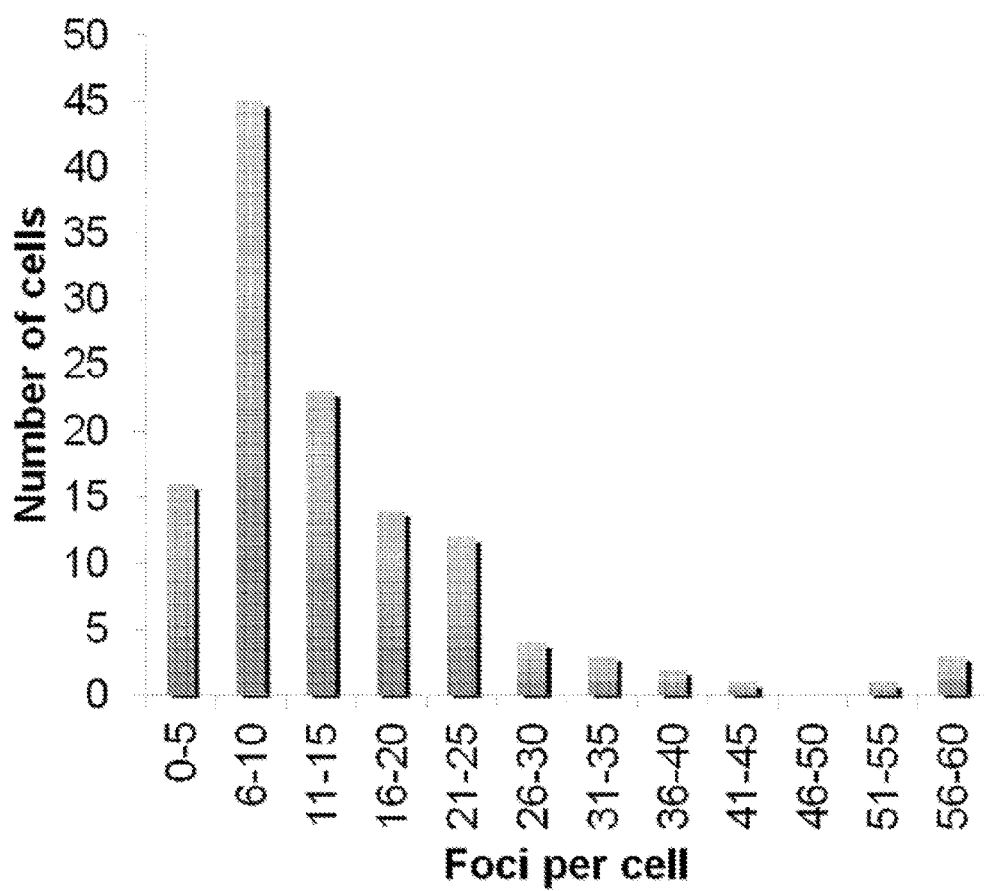

FIGS. 5a-5b: γH2AX foci analysis 24 h after radiation with 5Gy. Panel A shows control MRC5 cells, Panel B shows MRC5 cell pre-treated with targeted gold NPs. Increased levels of phosphorylated histone variant H2AX are a surrogate measure of increased levels of DNA double-strand breaks caused by DNA damaging agents (e.g. ionising radiation). This result demonstrates that nanoparticles targeted to the cell nucleus by a novel synthetic peptide consisting of gold attachment domain, nuclear targeting domain and DNA repaid inhibition domain in tandem configuration enhance cell killing by increasing the proportion of unrepaired/unrepairable DNA damage caused by radiation.

Figure 6A:
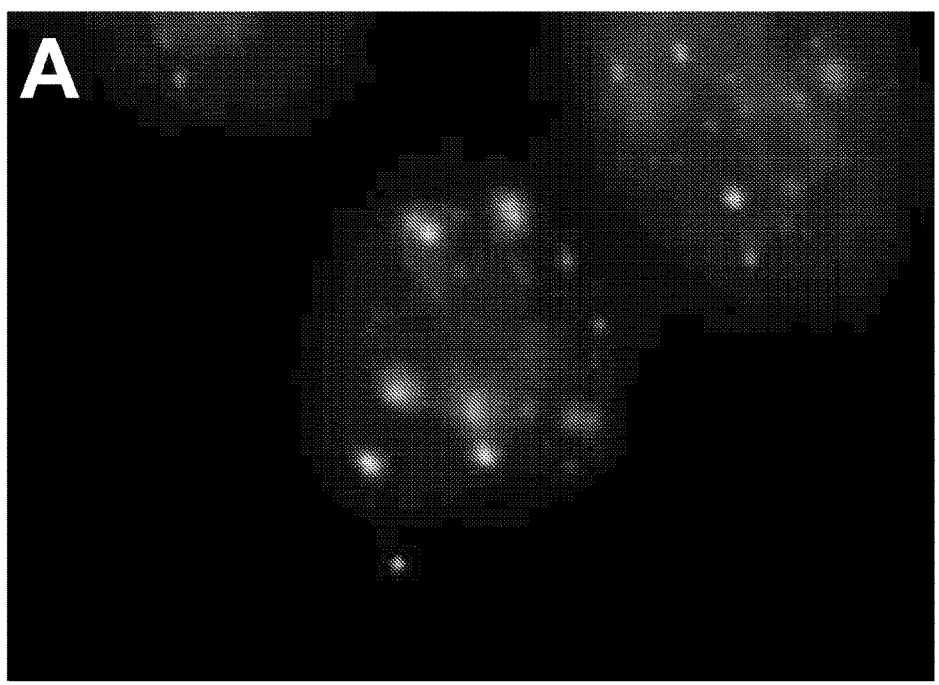
FIG. 6a-6c: Acentric chromosomal fragments (micronuclei) analysis 24 h after radiation with 5Gy.
Figure 6B:
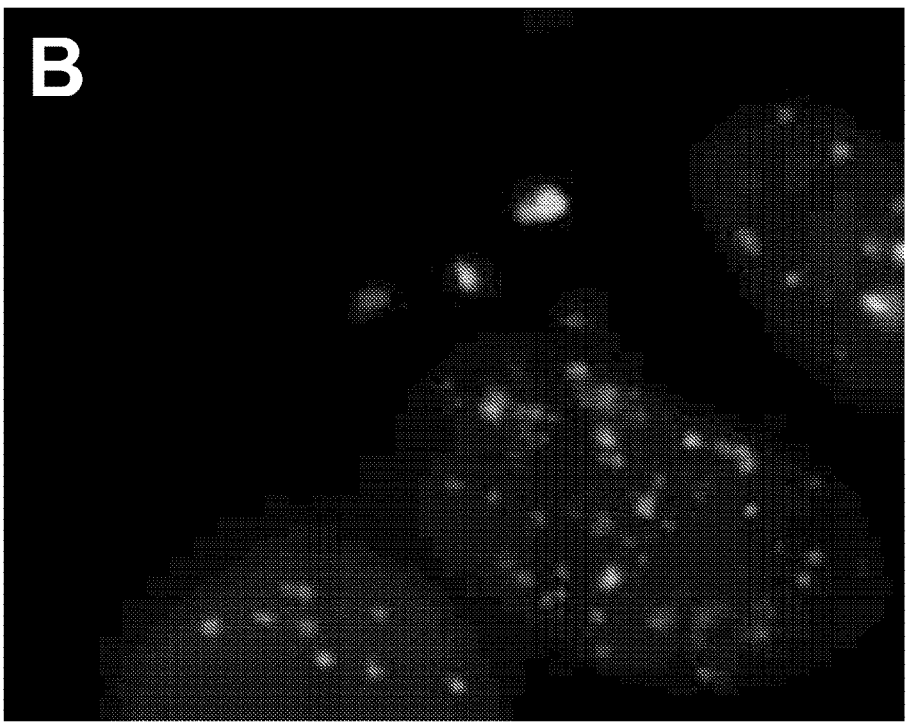
Figure 6C:
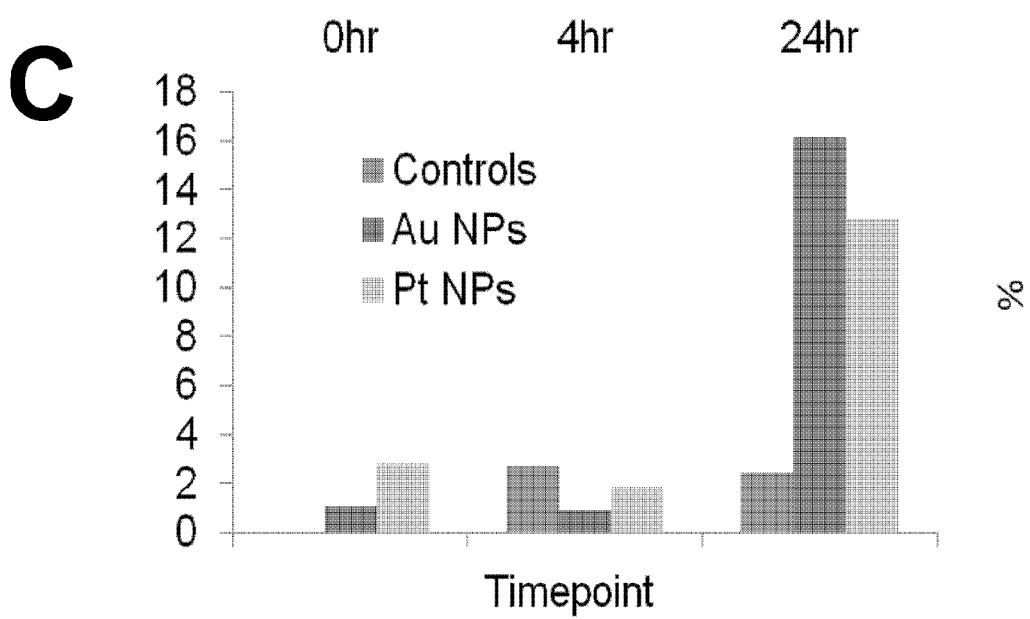

FIGS. 6a-6c: Acentric chromosomal fragments (micronuclei) analysis 24 h after radiation with 5Gy. Panel A shows control MRC5 cells, Panel B shows MRC5 cell pre-treated with targeted gold NPs, with 4 micronuclei clearly visible. Panel C summarises quantitative analysis based on 100 cells counted for each data set. The formation of micronuclei is indicative of higher levels of unrepairable DNA double-strand breaks. This result further demonstrates that nanoparticles targeted to the cell nucleus by a novel synthetic peptide consisting of gold attachment domain, nuclear targeting domain and DNA repair inhibition domain in tandem configuration enhance cell killing by increasing the proportion of unrepaired/unrepairable DNA damage caused by radiation.

Figure 7:
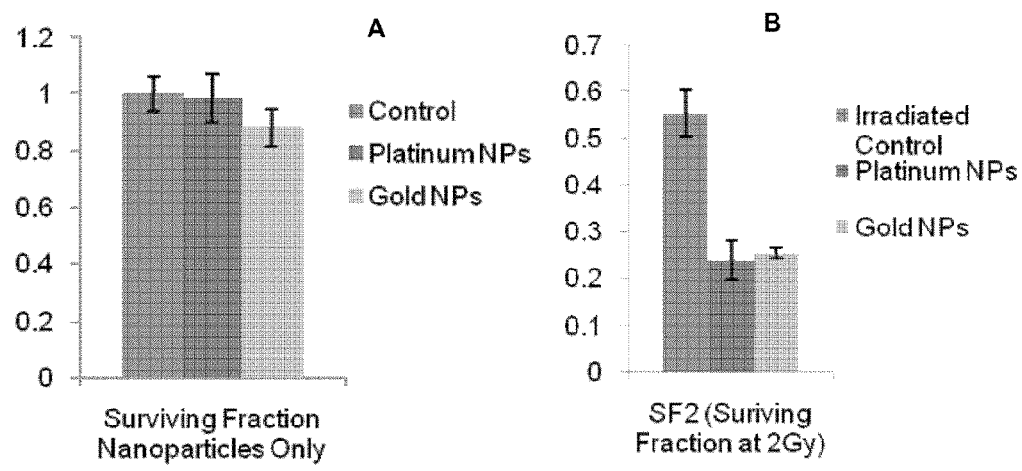
FIG. 7: Nanotoxocity analysis of targeted NPs as compared to synergistic effect with radiation on human cells.

FIG. 7: Nanotoxocity analysis of targeted NPs as compared to synergistic effect with radiation on human cells. Panel A: Clonogenic survival analysis of K562 human chronic myeloid leukaemia cells exposed to targeted gold and platinum NPs. Panel B: 2Gy survival fraction analysis in K562 human chronic myeloid leukaemia cells exposed to targeted gold and platinum NPs followed by 2Gy of ionising radiation. These results demonstrate that nanoparticles targeted to the cell nucleus by a novel synthetic peptide consisting of gold attachment domain, nuclear targeting domain and DNA repair inhibition domain in tandem configuration are not toxic for the targeted cells per se in the absence of DNA damaging agent.

Figure 8A:
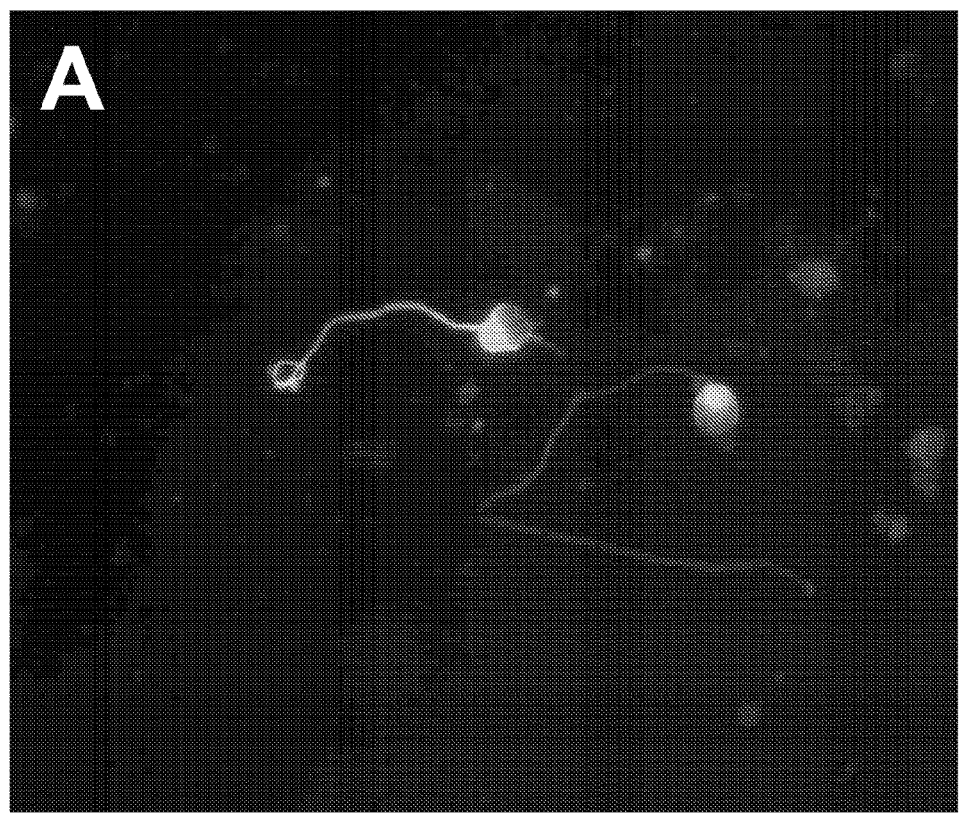
FIG. 8a-8c: A nano-neurotoxocity analysis of targeted NPs employing inhibition of central nervous system axon growth assay Panel A: Immuno-fluorescence analysis of axon growth in control ex vivo culture (the axon growth identified by green FITC label in all panels).
Figure 8B:
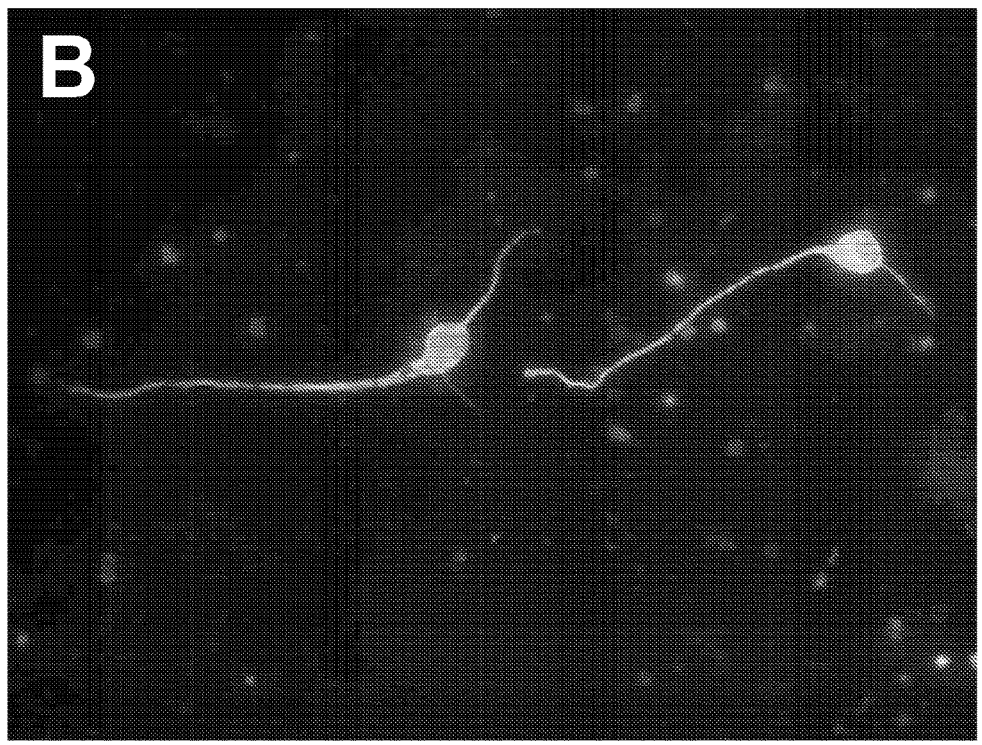
Figure 8C:
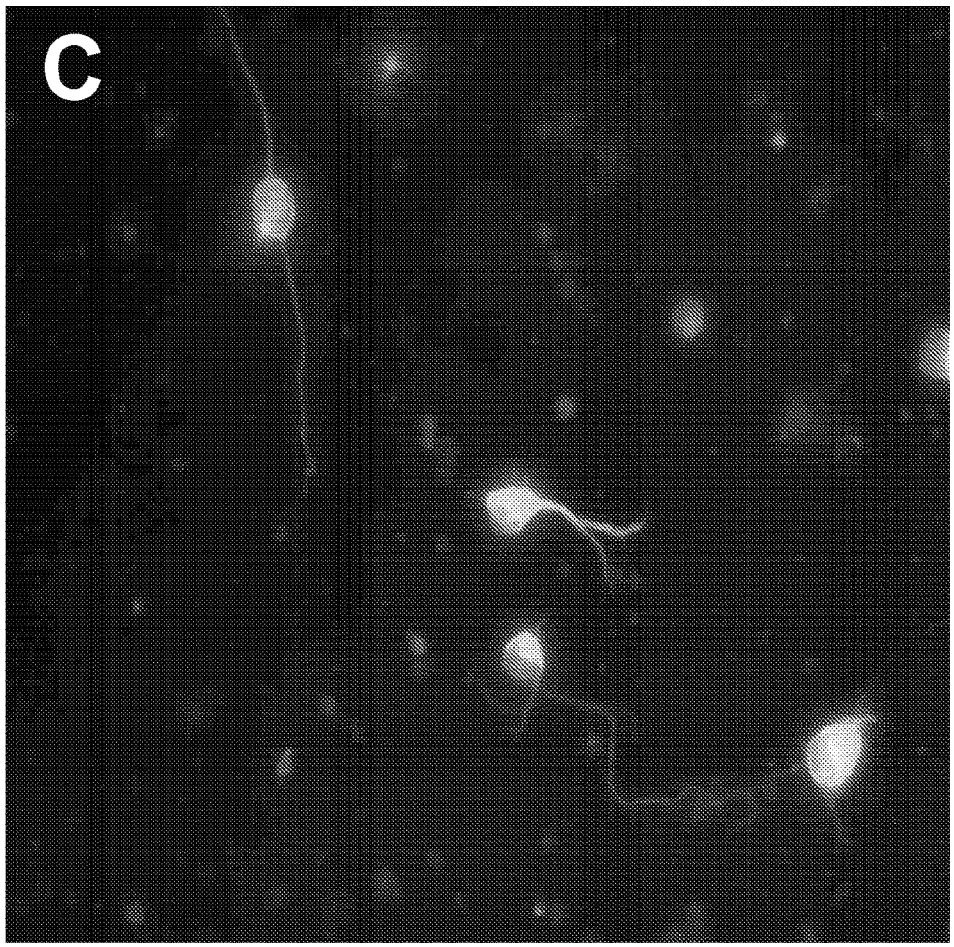

FIGS. 8a-8c: A nano-neurotoxocity analysis of targeted NPs employing inhibition of central nervous system axon growth assay Panel A: Immuno-fluorescence analysis of axon growth in control ex vivo culture (the axon growth identified by green FITC label in all panels). Panels B and C: Ex vivo neuron cultures exposed to gold (Panel B) and platinum (Panel C) targeted NPs. One of the clinically most relevant targets for using targeted nanoparticles are brain tumours, where the toxicity of the treatment to the healthy neuron tissues surrounding the tumour tissue is often a major problem. These results demonstrate that nanoparticles targeted to the cell nucleus by a novel synthetic peptide consisting of gold attachment domain, nuclear targeting domain and DNA repaid inhibition domain in tandem configuration are not toxic for the targeted neurons per se in the absence of DNA damaging agent.

Figure 9A:
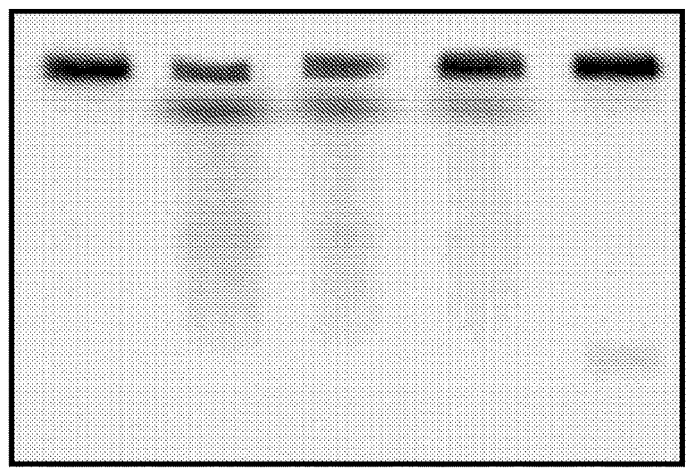
FIG. 9a-9b: Pulse field gel electrophoresis (PFGE) analysis of DSB repair kinetics in MRC5 human cells pre-treated with targeted gold and platinum nanoparticles (NPs) after irradiation with 30 Gy of γ-rays. Panel A: PFGE of irradiated control cells without NPs.
Figure 9A:
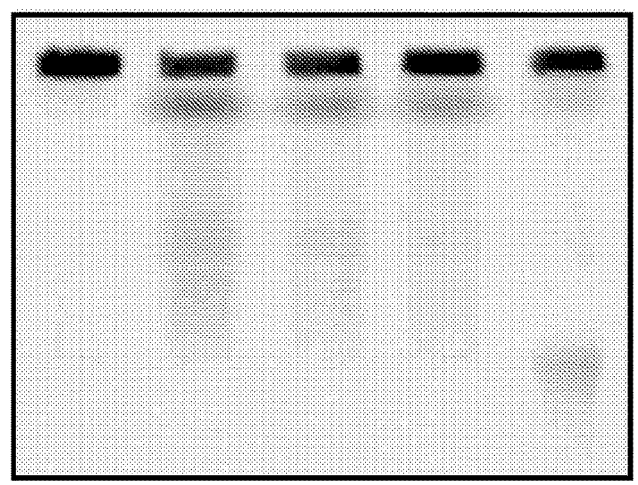
Figure 9B:
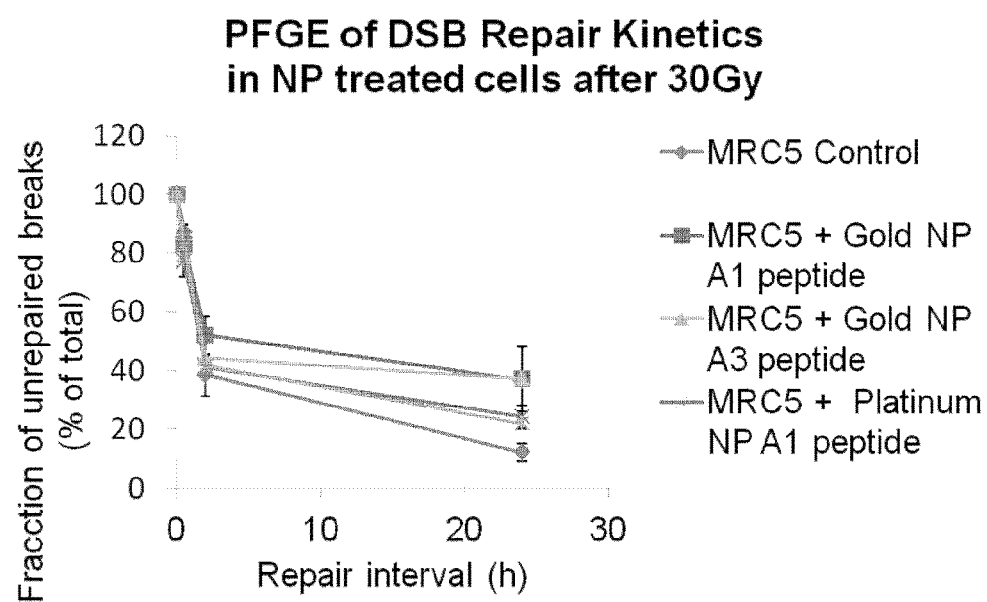

FIGS. 9a-9b: Pulse field gel electrophoresis (PFGE) analysis of DSB repair kinetics in MRC5 human cells pre-treated with targeted gold and platinum nanoparticles (NPs) after irradiation with 30 Gy of γ-rays. Panel A: PFGE of irradiated control cells without NPs. Panel B: PFGE of irradiated MRC5 cells pre-treated with gold targeted NPs. Panel C: quantitative analysis of DSB rejoining by PFGE. After 24 h repair time there is a highly significant increased in the percentage of unrepaired DSB in NPs treated cells compared to the controls following radiation (controls 12.03±3.11, gold A1 targeted 37.06±10.99, $p \leq 0.01$, gold A3 targeted 37.10±11.53, $p \leq 0.01$, platinum A1 targeted 24.13±4.03, $p \leq 0.01$, platinum A3 targeted 21.83±1.58, $p \leq 0.01$).

Using the assay that directly measures "broken DNA" these results demonstrate that nanoparticles targeted to the cell nucleus by novel synthetic peptides consisting of gold attachment domain, nuclear targeting domain and DNA repair inhibition domain in tandem configuration have a profound effect on DSB repair after exposure to ionising radiation, with many breaks left unrepaired after extensive period of repair time.

Materials and Methods

Preparation of Nanoparticles 13 nm gold and platinum citrate-coated nanoparticles (13 nmAuNPs, and 6 nmPtNPs, respectively) were prepared following known procedures [J. Phys. Chem. 90, 4765-4767 (1986), and Anal. Chem. 67, 735-743 (1995)]. Nanoparticles were then functionalised with novel tripartite peptides [Chem. Commun., 47, 6431-6433 (2011)]. Samples produced are listed in the tables below:

| Peptide Name | Components | Sequence |
|---|---|---|
| A1 | Attachment - M4-targetting - NBS1 inhibition | CALNNKKKKKKGGR GDMFGKEESLADDL |
| A3 | Attachment - Adenoviral NLS - NBS1 inhibition | CALNNGGFSTSLRA RKAKEESLADDL |

| Sample Name | Nanoparticle type |
|---|---|
| Au_A1 | 13 nm - gold nanoparticle - Peptide A1 |
| Au_A3 | 13 nm - gold nanoparticle - Peptide A3 |
| Pt_A1 | 6 nm - platinum nanoparticle - Peptide A1 |
| Pt_A3 | 6 nm - platinum nanoparticle - Peptide A3 |

Clonogenic Survival Assay

Normal human fibroblast cells MRC5VAs were maintained and subcultured in complete Dulbecco's Modified Eagle Medium (DMEM) containing 4.5 g/L D-Glucose, 2 mM L-glutamine, 1% v/v Penicillin/Streptomycin, 10% fetal bovine serum (FBS) (PAA labs), and 1% v/v non-essential amino acids (Invitrogen, Life Technologies). For the assay cells were harvested with 1× trypsin-EDTA (PAA labs) during mid-logarithmic growth (40-60% confluence). After trypsinisation, the cells were washed by centrifugation at 1500 rpm for 3 minutes, resuspended in medium and counted in a haemocytometer. The cells were then plated into 6-well plates at the required density, and placed in an incubator at 37° C. in a room-air atmosphere with 5% $CO_2$. After 24 hours to allow for reattachment, the cells were then loaded with nanoparticles at $5\times10^7$ NPs/cell. Untreated cells served as controls. After 24-hours the treated cells were trypsinised, washed by centrifugation, resuspended in medium, and counted. Stocks of the required number of cells for each dose of irradiation were aliquoted into fresh media, and placed on ice. Cells were irradiated to the required dose using a $^{137}$Cesium γ-source, at a dose rate of approximately 2.5 Gy/min. After irradiation the required number of cells for each dose were plated in triplicate into pre-warmed medium in 6-well plates. The plates were kept in an incubator undisturbed for 14 days. After the 14-day incubation period, colonies were fixed and stained using a 0.5% w/v Crystal violet solution in 50% methanol with water, and colonies counted. All conditions were done in triplicate; the survival experiments for each construct were repeated three times.

Histone H2AX Phosphorylation Assay and Micronuclei Analysis

MRC5VA normal human fibroblasts were grown attached to round cover slips in 24-well plates to almost confluent, and allowed to settle and reattach after seeding. After 24 hours, cells were treated with nanoparticles at $5\times10^7$ NPs/cell. Untreated cells served as controls. After 24 hours a single cover slip was removed for each construct to serve as an un-irradiated control. The remaining cover slips were placed on ice and irradiated to 5Gy using a $^{137}$Cesium γ-source, at a dose rate of approximately 2.5 Gy/min. After irradiation the cells were placed back into the incubator. At the relevant post-irradiation time-point, cells were permeabilised in ice-cold pre-extraction buffer (10 mM PIPES, pH 6.8, 300 mM Sucrose, 20 mM NaCl, 3 mM $MgCl_2$ and 0.5% Triton X-100) for seven minutes on ice. After washing in ice-cold phosphate buffered saline (PBS), cells were then fixed in 4% ice-cold paraformaldehyde, on ice for 10 minutes. Fixed cells were stored in PBS at 4° C. until all time points had been collected. Prior to immunostaining cells were washed in PBS, then incubated in blocking solution (10% FBS in PBS) at room temperature for 1 hour. After blocking cells were washed three times in PBS, before incubation with a 1:1000 dilution of mouse-anti γH2AX monoclonal (Millipore, UK) in 2% FBS in PBS for 1 hour at room temperature. Cells were washed three times in PBS before being incubated in a 1:1000 dilution of anti-mouse Alex Fluor 488 (Life Technologies) in 2% FBS in PBS for 1 hour at room temperature in the dark. Cells were washed in PBS and mounted in Vectashield with 4',6-diamidino-2-phenylindole (Vectorlabs, UK) and examined with a Zeiss microscope. The number of γH2AX foci were scored manually from stored images in a minimum of 50 nuclei, in triplicate. Cells with micronuclei were counted manually from the same images used for γH2AX foci analysis, at a minimum of 50 cells, in triplicate.

Bromodeoxyuridine Cell Proliferation Assay

For the assay MRC5VA cells were harvested, counted, and seeded into 25 $cm^2$ culture flasks (Corning, USA) at the required density. After allowing 24 hours for cells to recover and attach cells were loaded with nanoparticles at $5\times10^7$ NPs/cell. Unloaded cells served as a control. After 24 hours cells were pulsed labelled with the nucleotide analogue Bromodeoxyuridine (BrDU) for 20 minutes. Old medium containing the nanoparticles was removed and replaced with fresh medium containing 20 μM BrDU and placed in the incubator. After pulse labelling, cells were harvested by trypsinisation, and washed by centrifugation. The cell pellets were resuspended in complete DMEM, placed on ice, and irradiated to 5Gy using a $^{137}$Cesium γ-source, at a dose rate of approximately 2.5 Gy/min. After irradiation cells were re-distributed into 25 $cm^2$ flasks for harvesting at the required time-points.

At the required time-point cells were trypsinised, and washed twice in PBS by centrifugation. After the final wash, the supernatant was discarded and the cell pellet resuspended in the remaining drop of PBS, to prevent cells from clumping. Cells were then vortexed as 2 ml-20° C. 100% ethanol was added drip-wise. Fixed cells were stored at −20° C. until all samples had been collected. To stain, cells were first washed twice in PBS by centrifugation at 2000 rpm for 5 minutes. After the final wash cells were resuspended in 2 ml 2M hydrochloric acid containing 0.1 mg/ml pepsin and incubated at room temperature for 20 minutes. Cells were then washed three times in PBS by centrifugation at 2000 rpm for 5 minutes. After the final wash as much supernatant as possible was removed without disturbing the cell pellet. The cells were then resuspended in 100 μl PBS containing 0.5% normal goat serum, 0.5% Tween-20 (PNT), and mouse anti-BrDU monoclonal diluted at 1:50 (Dako, UK), and incubated for one hour at room temperature. Cells were washed three times in PBS by centrifugation, after the third wash as much supernatant as possible was moved from the cell pellet. The cells were then resuspended in 100 μl PNT containing anti-mouse Alexa Fluor 488 diluted at 1:50 (Life Technologies, UK), and incubated for 60 minutes at room temperature in the dark. Cells were washed in PBS by centrifugation once and resuspended in 0.5 ml PBS containing 10 μg/ml propidium iodide, and stored at 4° C. overnight in the dark overnight. Flow cytometric analysis was performed on a FACScalibur instrument (Becton Dickson, USA), and cell cycle analysis performed using FlowJo software (Tree Star, USA).

Pulse-Field Gel Electrophoresis

MRC5VA cells were harvested, counted, and seeded into 25 cm$^2$ culture flasks (Corning, USA) at the required density. After allowing 24 hours for cells to recover and attach, the exponentially growing cells were radioactively labelled by replacement of the old medium with fresh, complete DMEM supplemented with 0.02 μCi/ml $^{14}$C-Thymidine (Perkin Elmer). After 24 hours, without changing the medium, cells were loaded with nanoparticles at 5×10$^7$ NPs/cell. Unloaded cells served as a control. After a further 24 hours cells in stationary phase had the medium replaced with fresh complete DMEM for a 2-hour chase period. Cells were then trypsinised, and washed in pre-warmed PBS by centrifugation at 1500 rpm for 3 minutes. The supernatant was removed and the cells resuspended in 1 ml pre-warmed PBS and counted. The required number of cells were then pelleted by centrifugation and resuspended to the required volume of pre-warmed PBS and mixed gently with an equal volume of a 1% solution of low melting point agarose in PBS (LMPA), at a final density of 2.5-3.0×10$^6$ cells/ml. The suspension of cells in agarose was pipetted into a reusable plug mould (Bio-Rad). The mould was then placed at 4° C. for 15 minutes to solidify the agarose plugs. After setting, each plug was cut with sterile glass cover slips into 3 inserts. Inserts were transferred to 20× volume of complete DMEM and incubated on ice for 30 minutes. Inserts, except non-irradiated controls, were then irradiated to 30Gy using a $^{137}$Cesium γ-source, at a dose rate of approximately 2.5 Gy/min. After irradiation, inserts were poured into 6-well plates with pre-warmed complete DMEM and incubated at 37° C. in a room air atmosphere with 5% $CO_2$. At the required time-points the cells were lysed, by replacing the medium with 15× volume of lysis solution (0.5M EDTA, 1% N-laurolysarcosine, 1 mg/ml proteinase K), and incubating at 50° C. for 48 hours. After lysis, DNA samples in agarose inserts were extensively washed 5 times in 500× volume of TE buffer, pH 8.0 (10 mM Tris-HCl, 1 mM EDTA) to avoid remaining proteinase K and detergent contamination. Washed plugs were then stored in 20× volume TE buffer at 4° C. until electrophoresis.

Pulse-field gel electrophoresis was carried out on a 0.8% ultrapure agarose gel (BioRad), cast with 0.5×TBE buffer (50 mM Tris, 45 mM Boric acid, 0.5 mM EDTA) (BioRad). The agarose inserts containing the samples were gently placed into the wells of the gel and were pushed to the bottom of the well to avoid the formation of air bubbles. After loading, the inserts were sealed in the wells with 0.5% LMPA. The gel was then placed into the Bio-Rad CHEF-DR III apparatus. The gel was run for 48 hours at 1.5 volts/cm, with a switch time of 1800 seconds, an angle of 120°, in 0.5×TAE at 14° C. After electrophoresis, the gel was dried using a suitable gel dryer for approximately 6 hours at 50° C. onto positively charged filter paper, exposed to a storage phosphor screen for 48 hours, and analysed using a suitable phosphorimager.

Results

FIG. 1 shows that the targeted nanoparticles reach the cell nucleus. Non-targeted particles do not reach the cell nucleus.

FIG. 2 shows that targeted nanoparticles may be used in a variety of different cell populations. The particles enhance cell killing using radiation (FIG. 3).

This appears to be due to decreased DNA repair and increased unrepaired DNA damage due to the nanoparticles as shown by FIG. 4. This is confirmed by the observations of increased phosphorylated histone variant H2AX shown in FIG. 5. Higher level of DNA double strand breaks (dsb) were also observed using targeted nanoparticles (FIG. 6). Dsbs are difficult to repair and are often lethal in cells.

The targeted nanoparticles themselves do not appear to be toxic, per se, in the absence of the DNA damaging agent (FIG. 7) in all cell systems tested. This allows, for example, the nanoparticles to be administered and a focused area of cells to be targeted with, for example, a focused beam of ionizing radiation, with limited effects on surrounding cells. The nanoparticles appear to be non-toxic against neurons.

The effects of the nanoparticles on the repair of DNA dsb is persistent and long-lived. The targeted nanoparticles increase the time taken to repair dsb (FIG. 9), thus increasing the likelihood that the targeted cells will die.

The invention claimed is:

1. A radio- or chemo-sensitizing compound comprising
   (i) a nanoparticle;
   (ii) a DNA repair inhibitor; and
   (iii) a nuclear localization signal element (NLS);
   wherein the DNA repair inhibitor is attached to the nanoparticle, directly or via a linker moiety, and the NLS is attached to the DNA repair inhibitor or the linker moiety.

2. The compound of claim 1, wherein the DNA repair inhibitor is an inhibitor of double-strand break repair.

3. The compound of claim 1, wherein the DNA repair inhibitor is NBS1, Ku70, PARP1, H1x, or a fragment of any of the foregoing capable of inhibiting DNA repair, or a DNA phosphokinase inhibitor or a fragment thereof capable of inhibiting DNA repair.

4. The compound of claim 1, wherein the NLS is an adenoviral or SV40 NLS, or a synthetic NLS.

5. The compound of claim 1, wherein the nanoparticle is a metal nanoparticle.

6. The compound of claim 5, wherein the nanoparticle is gold, platinum or palladium or mixtures thereof.

7. The compound of claim 5, wherein the DNA repair inhibitor is attached to the nanoparticle via a linker moiety, and the linker moiety has an affinity for the metal nanoparticle.

8. The compound of claim 7, wherein the linker moiety is selected from the group consisting of thioctic acid, gold binding peptide 1 (GBP1), 3R-GBP1, CALNN peptide and glutathione.

9. The compound of claim 1, additionally comprising one or more moieties selected from the group consisting of a chemotherapeutic agent, bleomycin, doxorubicin, camptothecin, a DNA cross-linking agent, cis-platinin, an imaging agent, a contrasting agent, a vitamin, and a surface targeting agent.

10. A method for treating a cancer in a subject, the method comprising the step of administering to the subject a therapeutically effective amount for treating cancer of the compound of claim 1.

11. The method of claim 10 further comprising the step of treating the subject with radiotherapy.

12. A radio- or chemo-sensitizing compound comprising
    (i) a nanoparticle;
    (ii) a DNA repair inhibitor; and
    (iii) a nuclear localization signal element (NLS);
    wherein the IN is attached to the nanoparticle, directly or via a linker moiety, and the DNA repair inhibitor is attached to the NLS or the linker moiety.

13. The compound of claim 12, wherein the DNA repair inhibitor is NBS1, Ku70, PARP1, H1x, or a fragment of any of the foregoing capable of inhibiting DNA repair, or a DNA phosphokinase inhibitor or a fragment thereof capable of inhibiting DNA repair.

14. The compound of claim 12, wherein the NLS is an adenoviral or SV40 NLS, or a synthetic NLS.

15. The compound of claim 12, wherein the nanoparticle is a metal nanoparticle.

16. The compound of claim 15, wherein the nanoparticle is gold, platinum or palladium or mixtures thereof.

17. The compound of claim 15, wherein the NLS is attached to the nanoparticle via a linker moiety, and the linker moiety has an affinity for the metal nanoparticle.

18. The compound of claim 17, wherein the linker moiety is selected from the group consisting of thioctic acid, gold binding peptide 1 (GBP1), 3R-GBP1, CALNN peptide and glutathione.

19. The compound of claim 12, additionally comprising one or more moieties selected from the group consisting of a chemotherapeutic agent, bleomycin, doxorubicin, camptothecin, a DNA cross-linking agent, cis-platinin, an imaging agent, a contrasting agent, a vitamin, and a surface targeting agent.

20. A method for treating a cancer in a subject, the method comprising the step of administering to the subject a therapeutically effective amount for treating cancer of the compound of claim 12.

21. The method of claim 20 further comprising the step of treating the subject with radiotherapy.

22. A radio- or chemo-sensitizing compound comprising
    (i) a nanoparticle;
    (ii) a DNA repair inhibitor; and
    (iii) a nuclear localization signal element (NLS);
    where the DNA repair inhibitor and the NLS are each attached to the nanoparticle; and
    additionally comprising a DNA cross-linking agent, wherein the DNA cross-linking agent is cis-platinin.

* * * * *

UNITED STATES PATENT AND TRADEMARK OFFICE
CERTIFICATE OF CORRECTION

PATENT NO. : 9,943,598 B2
APPLICATION NO. : 14/403804
DATED : April 17, 2018
INVENTOR(S) : Boris Kysela It is certified that error appears in the above-identified patent and that said Letters Patent is hereby corrected as shown below:

In the Claims

In Claim 12, Column 14, Line 15, "wherein the IN is attached" should read -- wherein the NLS is attached --.

Signed and Sealed this
Twelfth Day of June, 2018

Andrei Iancu
*Director of the United States Patent and Trademark Office*